United States Patent
Hager et al.

(10) Patent No.: US 11,777,940 B2
(45) Date of Patent: Oct. 3, 2023

(54) STORING AND ACCESSING MEDICAL DATASETS ON THE BLOCKCHAIN

(71) Applicant: Siemens Healthcare GmbH, Erlangen (DE)

(72) Inventors: Florian Hager, Erlangen (DE); Christoph Pedain, Munich (DE); Benedikt Krueger, Ebensfeld (DE)

(73) Assignee: Siemens Healthcare GmbH, Erlangen (DE)

(*) Notice: Subject to any disclaimer, the term of this patent is extended or adjusted under 35 U.S.C. 154(b) by 221 days.

(21) Appl. No.: 16/960,664

(22) PCT Filed: Jan. 11, 2019

(86) PCT No.: PCT/EP2019/050686
§ 371 (c)(1),
(2) Date: Jul. 8, 2020

(87) PCT Pub. No.: WO2019/138071
PCT Pub. Date: Jul. 18, 2019

(65) Prior Publication Data
US 2020/0358782 A1    Nov. 12, 2020

(30) Foreign Application Priority Data
Jan. 12, 2018    (EP) .................... 18151466

(51) Int. Cl.
*H04L 9/40* (2022.01)
*G16H 10/60* (2018.01)
*G06F 16/9035* (2019.01)

(52) U.S. Cl.
CPC ........ *H04L 63/102* (2013.01); *G06F 16/9035* (2019.01); *G16H 10/60* (2018.01); *H04L 63/0823* (2013.01); *H04L 63/20* (2013.01)

(58) Field of Classification Search
CPC ..... H04L 63/102; H04L 63/0823; H04L 9/50; G06F 16/9035; G06F 21/645; G06F 21/33; G16H 10/60
See application file for complete search history.

(56) References Cited

U.S. PATENT DOCUMENTS

2009/0132813 A1* 5/2009 Schibuk ............ G06Q 20/4014
726/9
2012/0323750 A1   12/2012 Sivaramakrishnan et al.
(Continued)

FOREIGN PATENT DOCUMENTS

CN    103597489 A    2/2014
CN    107241360 A    10/2017

OTHER PUBLICATIONS

Das, Reenita: "Does Blockchain Have A Place In Healthcare?"; in: Forbes.com; May 2017; https://www.forbes.com/sites/reenitadas/2017/05/08/does-blockchain-have-a-place-in-healthcare/amp/; snapshot from Nov. 12, 2017.
(Continued)

*Primary Examiner* — Khoi V Le
(74) *Attorney, Agent, or Firm* — Harness, Dickey & Pierce, P.L.C.

(57) ABSTRACT

Methods are disclosed for setting up a microservice, enhancing a ledger of microservices with a further microservice and accessing medical datasets stored in a microservice. The microservice contains the medical dataset in an encrypted form. The microservice includes an access logic based on accessing entity information. The access logic defines access conditions to the medical dataset and is configured to grant access to the medical dataset upon the access conditions being fulfilled.

20 Claims, 15 Drawing Sheets

(56) References Cited

U.S. PATENT DOCUMENTS

2017/0222814 A1* 8/2017 Oberhauser ........ G06Q 20/4014
2017/0230349 A1* 8/2017 Gaur .................... G06F 21/629

OTHER PUBLICATIONS

"PKI based identity on a blockchain"; in: beame.io-Blog; Aug. 15, 2017;.
Jamsrandorj Uurtsaikh: "Oecentralizeo Access Control Using Blockchain"; XP055486025; pp. 1-78.
Blockchain Bundesverband e.V.:"Blockchain"; Kapitel 5: Gesundheitssystem; Okt. 2017 http://bundesblock.de/wp-content/uploads/2017/10/bundesblock_positionspapier_v1.1.pdf; and English translation thereof.
MintHealth Announces Vidamints (VIDA) to Align Stakeholders in a New Healthcare Ecosystem; in: BusinessWire.com; https://www.businesswire.com/news/home/20171205005079/en?wt.mc_id=AID631296_QSG_SCL_210505; Nov. 12, 2017.
Microservices—Wikipedia; Version from Nov. 14, 2017 https://en.wikipedia.org/w/index.php?title=Microservices&oldid=810315242.
Minthealth; https://www.minthealth.io/; Dec. 11, 2017.
E-Estonia Health records; https://e-estonia.com/solutions/healthcare/e-health-record/; Dec. 11, 2017.
https://patientery.com/ Dec. 11, 2017.
International Search Report PCT/ISA/210 for International Application No. PCT/EP2019/050686 dated Feb. 25, 2019.
Written Opinion of the International Searching Authority PCT/ISA/237 for International Application No. PCT/EP2019/050686 dated Feb. 25, 2019.

* cited by examiner

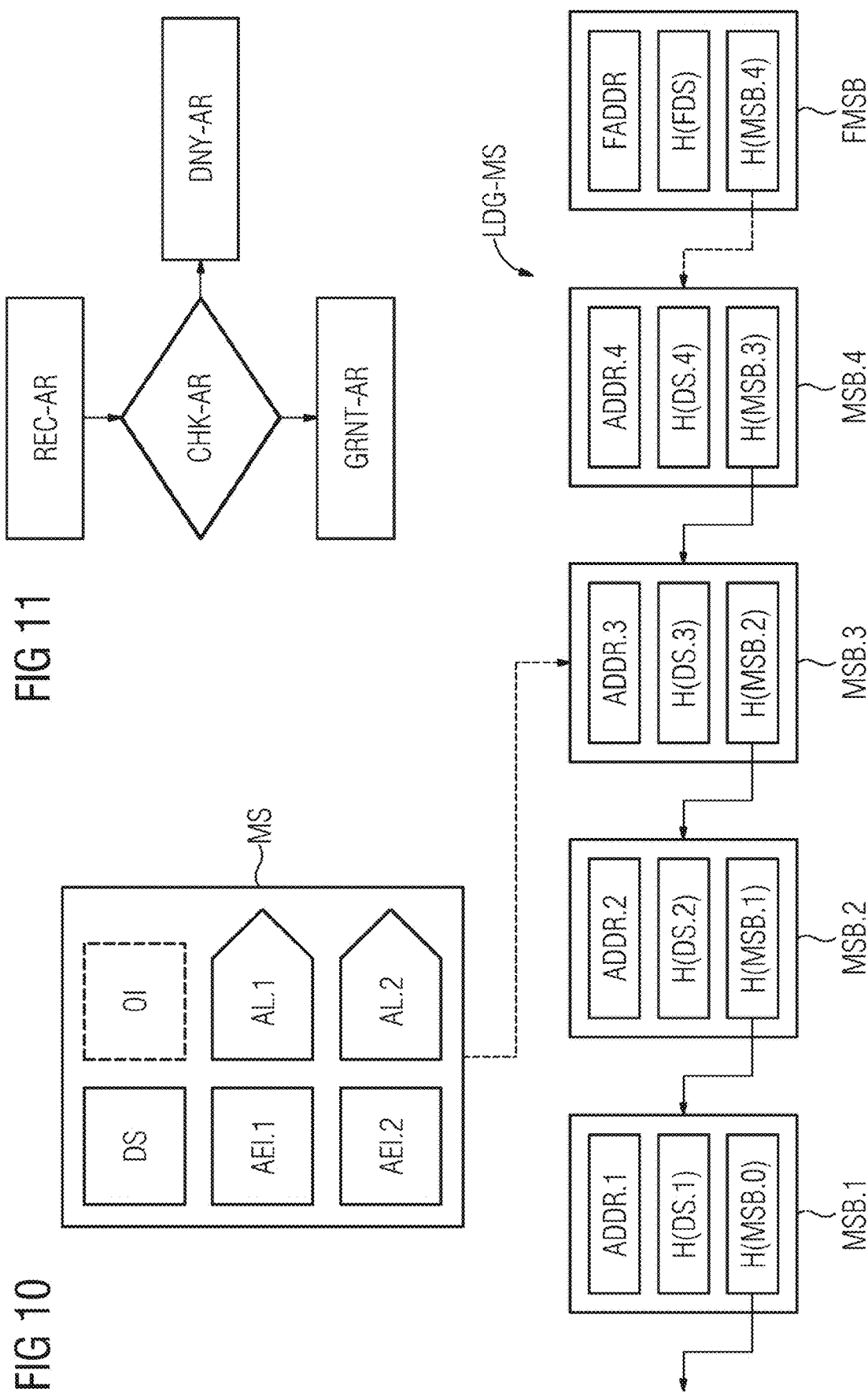

STORING AND ACCESSING MEDICAL DATASETS ON THE BLOCKCHAIN

PRIORITY STATEMENT

This application is the national phase under 35 U.S.C. § 371 of PCT International Application No. PCT/EP2019/050686 which has an International filing date of Jan. 11, 2019, which designated the United States of America and which claims priority to European patent application no. EP 18151466.2 filed Jan. 12, 2018, the entire contents of each of which are hereby incorporated herein by reference.

FIELD

Embodiments of the present application generally relate to storing and accessing medical data on the blockchain.

BACKGROUND

Storing and accessing medical data is connected with certain challenges: For example, medical data can be relevant over a long period of time, i.e. up to the lifespan of the patient or even beyond. At the same time, medical data can be generated by multiple parties and can utilize multiple different data formats, each with lifespans that might not coincide with the lifespan of the relevance of the medical data. Medical data can be owned by one or more parties. It can also be necessary for multiple parties to use medical data at multiple different locations. Such usage might not be restricted only to one particular use case. The relevance of a particular piece of medical data might change based on the use case in combination with external factors, such as the presence or absence of an emergency situation.

Furthermore, medical data contain most private and confidential aspects of a patient. Therefore, it must be ensured that medical data are stored in a secured way and that medical data cannot be accessed by unauthorized members of the public. Societies can change their view on availability and confidentiality of medical data, even in a rapid fashion. It is also possible that at any given moment, nations may add or relieve laws that restrict access and define ownership of medical data.

Current technologies attempt to provide medical data to its consumers by giving selective access to centralized storage facilities. This approach typically needs databases protected from unauthorized access at their perimeter which is individual to a specific database or facility. Furthermore, central management of credentials is typically needed by this approach. Therefore, such storage of medical data and access management to medical data can lead to increase vulnerability to attacks as it provides a large attack surface. Furthermore, accessing multiple medical datasets and creating patient histories across databases needs the creation of yet another database that consolidates the information, and requires the creation of links between these databases, which again represents a security risk. Managing access rights to medical data across facilities can pose technical problems and can lead to compromises in terms of security.

SUMMARY

At least one embodiment of the present application provides improved storage of medical data and/or improved management of access permissions to medical data.

Embodiments of the present application are directed to a method for setting up a microservice, a method for enhancing a ledger; a method for accessing a medical dataset contained by a microservice in an encrypted form; a method for accessing information stored in a digital twin; a setting up unit; an enhancing unit; an accessing unit; a digital twin accessing unit; a medical apparatus; a computer program product; and a computer-readable medium. Embodiments of the invention are contained in the claims and in the description.

In the following, embodiments of the invention are described with respect to the systems as well as with respect to the methods, in particular with respect to the setting up unit as well as with respect to the method for setting up a microservice; with respect to the enhancing unit as well as with respect to the method for enhancing a ledger; with respect to the accessing unit for accessing a medical dataset contained by a microservice as well as with respect to the method for accessing a medical dataset contained by a microservice; and with respect to the accessing unit for accessing information stored in a digital twin as well as with respect to the method for accessing information stored in a medical twin. Features, advantages or alternative embodiments herein can be assigned to the other claimed objects and vice versa. In other words, claims and embodiments for the units can be improved with features described or claimed in the context of the method, and vice versa. In this case, the functional features of the method are embodied by objective subunits of the units.

In one embodiment, the invention relates to a method for setting up a microservice, comprising the step of receiving a medical dataset, furthermore comprising the step of receiving accessing entity information describing an accessing entity, furthermore comprising the step of setting up the microservice based on the accessing entity information, wherein the microservice contains the medical dataset in an encrypted form, wherein the microservice comprises an access logic based on the accessing entity information, and wherein the access logic defines access conditions to the medical dataset and is configured to grant access to the medical dataset if the access conditions are fulfilled.

The invention relates in one embodiment to a method for accessing a medical dataset contained by a microservice in an encrypted form, wherein the microservice comprises an access logic based on an accessing entity information describing an accessing entity, wherein the access logic defines access conditions to the medical dataset, wherein the method comprises the step of receiving an access request to the medical dataset by a requesting entity, wherein the method furthermore comprises the step of performing a check if the access conditions are met by the requesting entity, and wherein the method furthermore comprises the step of granting access to the medical dataset to the requesting entity depending on the result of the check.

The invention relates in one embodiment to a method for accessing information stored in a digital twin, wherein the digital twin comprises information about a real-world source, wherein a profile is assigned to the digital twin and wherein the profile defines access to a subset of the information stored in the digital twin, wherein the profile is configurable by the real-world source, wherein the method comprises the step of receiving an access request to the subset of information stored in the digital twin by a requesting entity, wherein the method furthermore comprises the step of performing a check if the requesting entity is subject to the profile, and wherein the method furthermore comprises the step of granting access to the subset of information stored in the digital twin depending on the result of the check.

The invention relates in one embodiment to a setting up unit for setting up a microservice, comprising the following units:

interface, configured for receiving a medical dataset, furthermore configured for receiving accessing entity information describing an accessing entity, calculation unit, configured for setting up the microservice based on the accessing entity information, wherein the microservice contains the medical dataset in an encrypted form, wherein the microservice comprises an access logic based on the accessing entity information and wherein the access logic defines access conditions to the medical dataset and is configured to grant access to the medical dataset if the access conditions are fulfilled.

The invention relates in one embodiment to a computer program product comprising a computer program, the computer program being loadable into a memory unit of a setting up unit, including program code sections to make the setting up unit execute the method for setting up a microservice according to an embodiment of the invention when the computer program is executed in the setting up unit.

The invention relates in one embodiment to a computer-readable medium, on which program code sections of a computer program are saved, the program code sections being loadable into and/or executable in a setting up unit to make the setting up unit execute the method for setting up a microservice according to an embodiment of the invention when the program code sections are executed in the setting up unit.

The invention relates in one embodiment to an enhancing unit for enhancing a ledger with a further microservice, comprising the following units:

interface configured for receiving the ledger, wherein the ledger contains microservices, wherein each of the microservices contains a medical dataset in an encrypted form and comprises an access logic to the medical dataset, furthermore configured for receiving a further medical dataset, calculation unit configured for providing the further microservice containing the further medical dataset in an encrypted form and comprising an access logic to the further medical dataset, furthermore configured for including the further microservice into the ledger.

The invention relates in one embodiment to an accessing unit for accessing a medical dataset contained by a microservice in an encrypted form, wherein the microservice comprises an access logic based on an accessing entity information describing an accessing entity, wherein the access logic defines access conditions to the medical dataset, wherein the accessing unit comprises the following units:

interface, configured for receiving an access request to the medical dataset by a requesting entity, calculation unit, configured for performing a check if the access conditions are met by the requesting entity, furthermore configured for granting access to the medical dataset to the requesting entity depending on the result of the check.

The invention relates in one embodiment to a digital twin accessing unit for accessing information stored in a digital twin, wherein the digital twin comprises information about a real-world source, wherein a profile is assigned to the digital twin and wherein the profile defines access to a subset of the information stored in the digital twin, wherein the profile is configurable by the real-world source, wherein the accessing unit comprises the following units:

interface, configured for receiving an access request to the subset of information stored in the digital twin by a requesting entity, calculation unit, configured for performing a check if the requesting entity is subject to the profile, furthermore configured for granting access to the subset of information stored in the digital twin depending on the result of the check.

BRIEF DESCRIPTION OF DRAWINGS

In the Following

FIG. 10 shows an embodiment of a ledger comprising microservice blocks, FIG. 11 shows a flowchart of an embodiment of a method for accessing a medical dataset contained by a microservice in an encrypted form.

DETAILED DESCRIPTION OF THE EXAMPLE EMBODIMENTS

Figure 1:
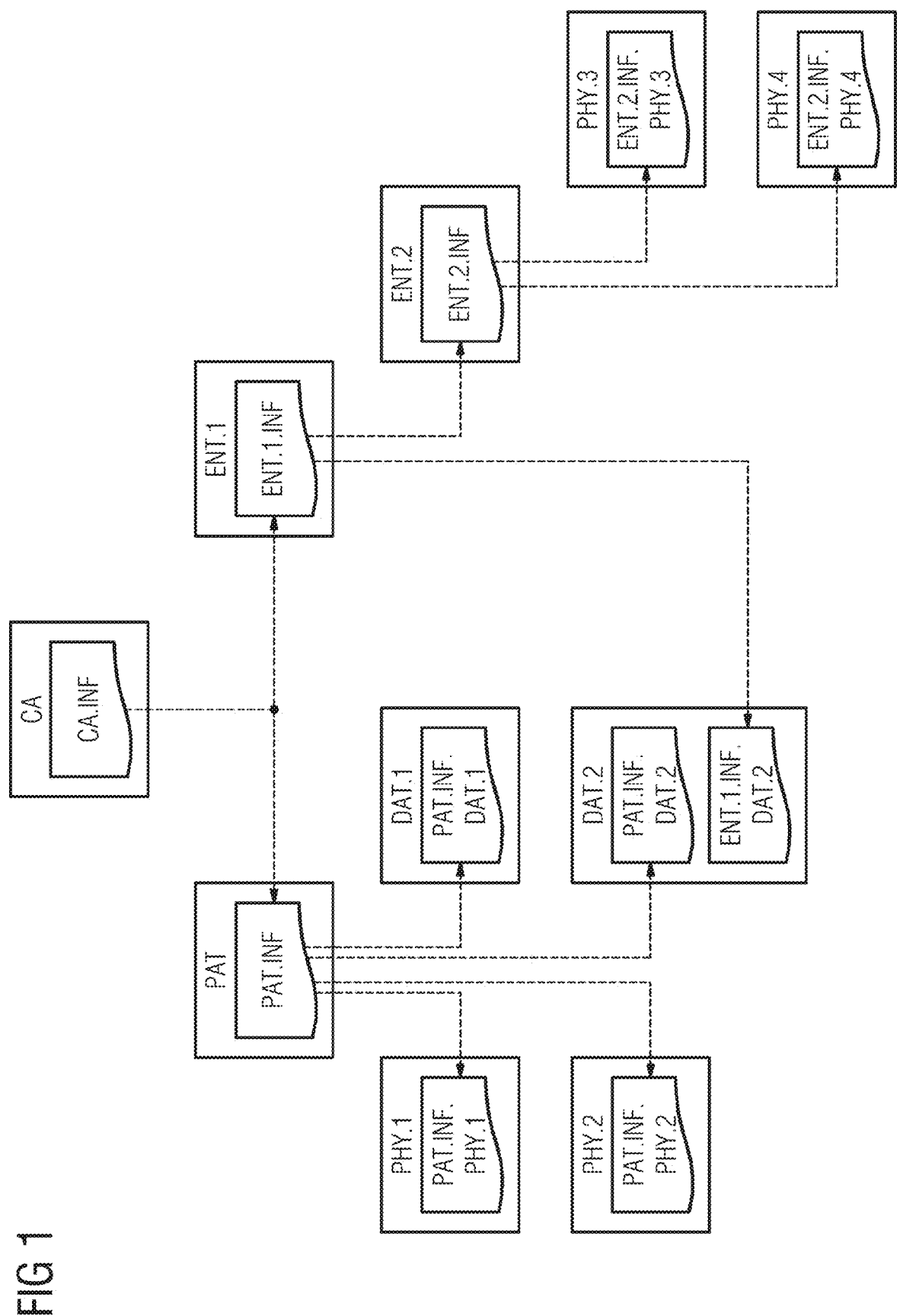
FIG. 1 shows a schematic view of a patient sharing data to multiple entities.

In one embodiment, the invention relates to a method for setting up a microservice, comprising the step of receiving a medical dataset, furthermore comprising the step of receiving accessing entity information describing an accessing entity, furthermore comprising the step of setting up the microservice based on the accessing entity information, wherein the microservice contains the medical dataset in an encrypted form, wherein the microservice comprises an access logic based on the accessing entity information, and wherein the access logic defines access conditions to the medical dataset and is configured to grant access to the medical dataset if the access conditions are fulfilled.

In particular, the step of receiving a medical dataset is executed by an interface, in particular by an interface of a setting up unit. In particular, the step of receiving accessing entity information is executed by the interface, in particular by the interface of the setting up unit. In particular, the step of setting up the microservice is executed by a calculation unit, in particular by a calculation unit of the setting up unit.

The step of receiving a medical dataset can be executed before or after the step of receiving accessing entity information, alternatively both steps can be performed at the same time or parallel. In particular, the step of setting up the microservice is executed after the step of receiving the medical dataset and after the step of receiving accessing entity information. Optionally, the method for setting up a microservice can furthermore comprise the step of providing the microservice. In particular, the step of providing the microservice is executed by the interface, in particular by the interface of the setting up unit.

The medical dataset generally comprises medical data of a patient or a group of patients or a population of patients.

The medical dataset can comprise a medical image dataset. Such medical image dataset is acquired from the patient using a medical imaging apparatus, e.g. a magnetic resonance apparatus, a single-photon emission tomography (SPECT) apparatus, a positron emission tomography (PET) apparatus, a computed tomography apparatus, an ultrasound apparatus, an X-ray apparatus, a C-arm apparatus or a combined medical imaging apparatuses formed by any combination composed of the aforementioned imaging modalities. The medical image dataset can also comprise automatically, semi-automatically or manually generated processing information, such as segmented organs, contour information, registration information, etc.

The medical dataset can also comprise medical data acquired or derived from other medical apparatuses which are not medical imaging apparatuses. Such other medical apparatuses can e.g. be a treatment apparatus, e.g. a radiotherapy device, a lithotripsy device, a laser treatment device, an infusion pump or an interventional treatment device. The medical data can also stem from an apparatus for intensive medicine, a mobile monitoring device, a respiratory device, an anesthetic machine, an ECG device, an EEG device, a blood pressure measurement device, an infusion device or a dialysis device. The medical dataset can also comprise laboratory diagnostics or genetic information.

The medical dataset can also comprise a complete or part of an electronic health record of a patient. Therefore, the medical dataset can comprise information about a disease history of the patient. The medical dataset can also contain annotation information, which describes automatically, semi-automatically or manually generated diagnostic findings in the medical dataset. The medical dataset can also comprise demographic metadata related to the patient, such as gender, age, weight, size, etc.

Other medical data which can be considered by those skilled in the art can also be part of the medical dataset.

The medical dataset may only be a pointer to a specific location in a storage database in which medical data are stored. This storage database can be a central database, cloud storage, or a distributed database. In this case, the pointer is contained by the microservice in an encrypted form. Access to the medical dataset means access to the pointer so that using the pointer the medical data which are stored in the storage database can be accessed.

The embodiments of the invention described could also be applied for datasets which are non-medical datasets or datasets in general, in this case a dataset comprises information about a real-world source. In other words, in this case the words "medical dataset" can be replaced with the word "dataset" throughout the specification and the claims.

Receiving the medical dataset typically comprises loading a medical dataset which has previously been acquired of a patient. The medical dataset is thereby normally retrieved from a database comprising multiple medical datasets. Such database can be a picture archiving and communication system (PACS) database. Such database can be embodied as cloud storage. The medical dataset can also be received directly from the medical imaging device which is used for acquiring the medical dataset. Receiving the medical dataset may also comprise an acquisition of the medical dataset using a medical imaging device.

Receiving the medical dataset may comprise receiving an already encrypted medical dataset, i.e. a medical dataset in an encrypted form. In this case, the encryption process is not part of the claimed method. Alternatively, a non-encrypted medical dataset can be received. Then, the encryption of the medical dataset can be performed as part of the claimed method, either as part of the receiving of the medical dataset or as part of setting up the microservice (see detailed description in one of the following paragraphs).

If the medical dataset is a pointer to a specific location in a storage database in which medical data are stored, then receiving the medical dataset typically comprises receiving the pointer in an encrypted or non-encrypted form.

The accessing entity typically is an entity which is allowed to access the medical dataset contained by the microservice. Such entity can be a group of persons, an individual person, a legal entity, a software component or a physical device. In particular cases, the accessing entity can be a certain group of medical practitioners, e.g. a group of emergency physicians. To provide further examples, the accessing entity can also be a medical clinic association, a hospital chain, a single hospital or a certain medical practice. The accessing entity can also be defined as the patient whom the medical dataset is acquired from. In particular, the accessing entity can also be different from the patient whom the medical dataset is acquired from (in other words, the patient the medical dataset relates to). The microservice can be based on more than one accessing entities.

The accessing entity information generally comprises information about the identity of the accessing entity. In that sense, the accessing entity information can comprise information that can be used to identify, to contact, or to locate the accessing entity.

The microservice can generally be regarded as an independently deployable service which can be used in a modular form. Therefore, the microservice typically is an autonomous process, in particular an autonomous application. Generally, the microservice comprises a virtual environment to run software. Furthermore, the microservice is typically characterized by its small and lightweight architecture. Such architecture of the microservice is typically reduced to a few core functionalities. The microservice can be set up, i.e. spun up or established, on demand. The microservice itself typically comprises different functionalities, especially related to storing the medical dataset in an encrypted form or to regulate access to the medical dataset contained by the microservice. In particular, a microservice can be implemented as a RESTful webservice ("REST" is an acronym for "Representational State Transfer"), in particular based on HTTP (acronym for "Hypertext Transfer Protocol") requests like HTTP GET or HTTP POST. In particular in this case, the term "microservice" can be replaced with "webservice" or "RESTful webservice" throughout the specification and the claims. In particular, the interaction of external applications with a webservice can be based on the REST protocol.

In particular, several microservices can be used or combined within a microservice architecture in order to create rich or complicated applications. In particular, an application implemented by a microservice architecture is not to be considered as a microservice itself.

Setting up the microservice based on the accessing entity information can comprise that the accessing entity information is used as an input variable during the setup of the microservice. The accessing entity information is then typically passed to the access logic of the microservice so that the access logic can be set up based on the accessing entity information. By setting up the microservice based on the accessing entity information, information which entity or which entities are allowed to access the medical dataset contained by the microservice can be provided to the microservice, in particular to the access logic of the microservice.

The microservice particularly contains, i.e. stores, the medical dataset in an asymmetrically encrypted form. Therefore, the medical dataset typically has been encrypted, e.g. using asymmetric/public key encryption, before it is stored in the microservice. It is also possible that the microservice itself contains encryption functionalities. In that case the encryption of the medical dataset typically is a part of the setup of the microservice. In particular cases, the medical dataset can also be contained by the microservice in a symmetrically encrypted form. The microservice containing the medical dataset in an encrypted form can also mean that the microservice just stores a pointer in an encrypted form. Such pointer then points to a specific location in a storage database in which medical data are stored The access logic typically is one of the core functionalities of the microservice. Generally, the access logic regulates access to the medical dataset which is contained by the microservice in an encrypted form. I.e. the access logic can validate access requests to the medical dataset. Furthermore, the access logic can grant or deny access to the medical dataset contained by the microservice. In particular, if a microservice is implemented as a RESTful webservice, the access logic can be executed or controlled by passing parameters to the RESTful webservice, in particular a separate parameter can be used containing data used as input for the access logical in access requests for the medical data contained in the microservice.

The access logic being based on the accessing entity information that the access logic is able to validate access credentials contained in the accessing entity information. Therefore, the access conditions to the medical dataset can be set based on the accessing entity information, in particular based on the access credentials.

The access conditions generally form the conditions under which the medical dataset contained by the microservice in an encrypted form can be accessed. A requesting entity can get access to the medical dataset if the access conditions are fulfilled. In that case, the requesting entity can load or view a content of the medical dataset in a decrypted form. Therefore, the microservice typically comprises an output functionality, e.g. an output application programming interface, which enables access to the medical dataset, in particular in a decrypted form. In case the medical dataset only contains a pointer to a specific location in a storage database in which medical data are stored, the requesting entity can access the medical data in the database the pointer points to.

The inventors have recognized that by at least one embodiment of the method different medical datasets of a patient, a group of patients or a population of patients can be stored in distributed databases formed by the microservices created with the proposed methods, while encryption of the medical datasets can be guaranteed on the level of such a microservice. So no protection of any network perimeter is required, and even in the event of a compromise of one microservice comprising one medical dataset, the encryption method and/or the encryption key of the compromised microservice cannot be used to access any other medical dataset contained in any other microservice. Furthermore there is no dependence on any particular cloud provider or datacenter.

Furthermore, by using an access logic based on accessing entity information within the microservice, flexible and secure access to the medical dataset can be granted based on the level of the single medical dataset, so it is possible to granularly grant access to single parts of the electronic medical record of the patient.

According to a further embodiment of the invention the medical dataset relates to a patient, and the accessing entity is different from the patient. In particular, the medical dataset also relates to the patient if the medical dataset relates to a group of patients comprising the patient or to a population of patients comprising the patient.

The inventors have recognized that granting access to an accessing entity being different to the patient the medical data relates to leverages the full potential of the proposed method. For only regulating the access of the patient to its own medical data no microservice-based access logic is necessary, because presumably a patient has access to all medical data relating to him or her.

According to a further embodiment of the invention, the accessing entity information comprises access credentials, which are stored related to the microservice, wherein the access logic defines the access conditions based on the access credentials wherein the access conditions are fulfilled if the access credentials are related to a requesting entity which requests access to the medical dataset.

The access credentials can serve to validate the identity of the accessing entity. Furthermore, the access credentials may also be able to validate information contained in the accessing entity information, e.g. the identity information of the accessing entity. The fact that the access credentials are stored related to the microservice particularly means that the access credentials are stored in a way so that the access logic can use the access credentials to validate access requests to the medical dataset contained by the microservice in an encrypted form. Therefore, the access credentials can also be stored within the microservice. The access credentials can directly define the access conditions in a way that only requesting entities which the access credentials are related to are granted access to the medical dataset. Therefore, the access credentials can be embodied as at least one digital certificate or at least one token or at least one key pair. Other forms of access credentials may also be implemented.

The requesting entity is the entity which requests access to the medical dataset. The requesting entity can be an entity selected from the list mentioned above regarding the accessing entity.

Whereas the accessing entity is the entity which is allowed to access the medical dataset, the requesting entity may be or may not be entitled to access the medical dataset contained by the microservice. The actual status of entitlement of the requesting entity to access the medical dataset can be determined by checking if the access credentials stored in the microservice are related to the requesting entity. The access credentials are generally related to the requesting entity if the identity of the requesting entity can be verified by the access credentials or credentials related to the access credentials.

The inventors have recognized that by using access conditions based on access credentials the requesting entity can be verified fast and easily by inspecting the access credentials.

According to a further embodiment of the invention, the access credentials are an access certificate and the access conditions are fulfilled if the access certificate is related to the requesting entity.

The access credentials can be formed by one or more access certificates. The access certificate is a digital certificate, i.e. a public key certificate or an identity certificate. The access certificate can be an electronic document relating to the ownership of a public key. The access certificate therefore usually contains information about the public key and the accessing entity related to this public key. Furthermore, the access certificate typically comprises a digital signature which verifies the certificate's content. In particular the digital signature is based on a private key related to a parent certificate.

A certificate generally belongs to an entity if the entity has access to the private key belonging to the certificate. Such private key belonging to the certificate generally is the counterpart the public key which the certificate contains information about. Therefore, the accessing entity typically has access to the private key of the access certificate if the access certificate belongs to the accessing entity. Furthermore, the microservice typically has access to the private key of the access certificate if the access certificate belongs to the microservice, in particular if such access certificate is stored in the microservice.

A first certificate is generally derived from a second certificate if the second certificate is a parent certificate for the first certificate. Therefore, the second certificate can digitally sign the first certificate, in particular using a private key related to the second certificate. It is also possible that the first certificate is digitally signed by a certificate authority, in particular using a private key using a certificate authority. In this case, the first certificate is derived from the second certificate if authorization information issued by the second certificate proves the first certificate to be derived from the second certificate. In particular, the authorization information can be documented in an access ledger. A certificate derived from the first certificate can be seen as derived from the second certificate as well. A first certificate is generally directly authorized by a second certificate if the first certificate is directly derived from the second certificate, in particular without any intermediate certificates, so that the second certificate is the direct parent certificate to the first certificate.

A certificate typically is related to the requesting entity if the identity of the requesting entity is verified by the certificate. The requesting entity can present a certificate identifying itself to the microservice, in particular the access logic of the microservice. If such identification certificate belonging to the requesting entity, i.e. a request certificate, proves the relation to corresponding certificate, the requesting entity can be entitled to access the medical dataset contained by the microservice.

The inventors have recognized that by using a certificate, in particular a digital certificate, identities and authorizations of entities can be checked reliably. Furthermore, by using certificates based on an asymmetric encryption system, identities and authorizations can be created and/or verified without relying on shared secrets, which makes it harder to manipulate the process of creating and/or verifying identities and authorizations, and which reduces the security threat originating from a discovery of a shared secret.

According to a further embodiment of the invention the access certificate is an X.509 certificate. The access certificate being a X.509 certificate means that the access certificate conforms to the X.509 standard. The inventors have recognized that by using X.509 certificates it is possible to use existing certificate infrastructure, which leads on the one hand to a cost-efficient implementation of the method, and on the other hand to a securer implementation due to the possibility of using already existing, well-tested components, e.g. hardware components and/or software libraries.

According to a further embodiment of the invention the access certificate belongs to the accessing entity and the access certificate is related to the requesting entity if the identity of the requesting entity is verified by the access certificate. In particular, the microservice can comprise a copy of the access certificate belonging to the accessing entity, and in particular, the microservice does not have access to the private key related the access certificate.

The inventors have recognized that by using an access certificate belonging to the accessing entity during the method step of setting up the microservice no action from the accessing entity is necessary. In other words, it is possible to set up a microservice without interaction with the accessing entity, which reduces the communication effort and prevents an overload of the accessing entity.

According to a further embodiment of the invention the access certificate belongs to the microservice and is derived from a certificate belonging to the accessing entity, and wherein the access certificate is related to the requesting entity if the identity of the requesting entity is verified by the certificate belonging to the accessing entity.

The inventors have recognized that by using an access certificate belonging to the microservice the set up microservice is independent from the status of the certificate belonging to the accessing entity. In particular, a compromitation or a revocation of the certificate belonging to the microservice not necessarily leads to a compromitation or a revocation of the access certificate.

According to a further embodiment of the invention the microservice comprises multiple access logics based on different accessing entity informations and defining different access conditions to the medical dataset. The inventors have recognized that by using multiple access logics access to the medical dataset contained in the microservice can be granted to different accessing entities, so it is not necessary to have different microservices for the same medical dataset. So the memory needed for storing microservices can be reduced. In particular, the access rights granted by the multiple access logics can be different. For example, for a first of the different accessing entities only a limited access (e.g. limited in time or limited in number of access) to the medical data contained in the microservice can be granted, wherein a second of the different accessing entities can be granted unlimited access to the medical data contained in the microservice.

According to a further embodiment of the invention the medical dataset relates to a patient, wherein a first of the different accessing entity informations relates to an accessing entity being different from the patient, and wherein a second of the different accessing entity informations relates to the patient. The inventors recognized that by including into the access logic the access of the patient and other entities, having the possibility to grant different access rights, the method and the microservices created by the method can be used for both the patient managing its own data and for other entities, without the need for setting up different access possibilities for the patient and the other entities.

According to a further embodiment of the invention, the step of receiving the medical dataset comprises the substep of receiving encryption information, and the substep of encrypting the medical dataset using asymmetric encryption based on the encryption information. In particular, the encryption information can be owner information describing the owner of the medical dataset. In particular, the substeps of receiving encryption information and the substep of encrypting the medical dataset can be executed separate from the interface and the calculation unit used in the method for setting up the microservice.

In this case, the medical dataset is received in a non-encrypted form and encryption of the medical dataset is performed as part of the claimed method, in particular previous to setting up the microservice. The asymmetrically encrypted medical dataset can then be passed to the microservice which can then store the medical dataset in an asymmetrically encrypted form.

The owner information generally serves to identify the owner of the medical dataset, i.e. the person which should have access to the medical dataset under any circumstances. The owner of the medical dataset generally is the patient of which the medical dataset has been acquired. The owner information typically comprises digital identification information, such as a private key which the medical dataset can be encrypted with.

The inventors have recognized that by using these substeps the medical dataset is only processed in an encrypted way by the method, and not in plaintext, which increases the security of the method.

According to a further embodiment of the invention, the step of setting up the microservice comprises the substep of receiving encryption information, and the substep of encrypting the medical dataset using asymmetric encryption based on the encryption information.

In particular, the encryption information can be owner information describing the owner of the medical dataset. In particular, the encryption information can be based on the accessing entity information, in particular on the access credentials, and in particular on the access certificate.

Also in this case, the medical dataset is received in a non-encrypted form and encryption of the medical dataset is part of the claimed method. In contrast to the previous embodiment the encryption of the medical dataset is not performed previous to setting up the microservice, but during the setup of the microservice. Therefore, the microservice comprises asymmetric encryption functionalities so that the microservice can encrypt the medical dataset so that the medical dataset can be stored in the microservice in an asymmetrically encrypted form.

The inventors have recognized that by using these substeps the encryption of the medical dataset is independent from the submitter of the medical dataset, which increases the security of the method. Furthermore, by encrypting during setting up the microservice the encryption can be more flexible, for example using different security levels for the encryption.

The invention relates in one embodiment to a method for enhancing a ledger with a further microservice, comprising the step of receiving the ledger, wherein the ledger contains microservices, wherein each of the microservices contains a medical dataset in an encrypted form and comprises an access logic to the medical dataset, furthermore comprising the step of receiving a further medical dataset, furthermore comprising the step of providing the further microservice containing the further medical dataset in an encrypted form and comprising an access logic to the further medical dataset, furthermore comprising the step of including the further microservice into the ledger.

In particular, the step of receiving the ledger is executed by an interface, in particular by an interface of enhancing unit. In particular, the step of receiving a further medical dataset is executed by the interface, in particular by the interface of the enhancing unit. In particular, the step of providing the further microservice is executed by a calculation unit, in particular by a calculation unit of the enhancing unit. In particular, the step of including the further microservice into the ledger is executed by the calculation unit, in particular by the calculation unit of the enhancing unit.

The step of receiving the ledger can be executed before or after the step of receiving the further medical dataset, alternatively both steps can be performed at the same time or parallel. In particular, the step of providing the further microservice is executed after the step of receiving the ledger and after the step of receiving the further medical dataset. In particular, the step of including the further microservice into the ledge is executed after the step of providing the further microservice. Optionally, the method for enhancing a ledger with a further microservice can furthermore comprise the step of providing the ledger, wherein the step of providing the ledger is executed after the step of including the further microservice into the ledger. In particular, the step of providing the ledger is executed by the interface, in particular by the interface of the enhancing unit.

The ledger, in particular a distributed ledger, is generally based on a database, in particular a decentralized database. The ledger comprises multiple records, i.e. database entries. The records are typically constructed and stored by multiple nodes of a network. The construction and maintenance of the records is typically not performed by a central authority, but independently by nodes of the network. In typical cases, all nodes of the network maintain one copy of the ledger. Updating the ledger is typically based on a consensus mechanism.

The microservices are typically contained by separate records, e.g. blocks, of the ledger. In particular, each microservice is assigned to a separate record of the ledger. In certain cases, it is also possible that more than one microservice is contained by one single record of the ledger. Of course, the ledger may not only comprise the microservices, but also further information or additional services, such as e.g. APIs or translators. Generally, the microservices are contained by the ledger in a compiled form.

Typically, a first record of the ledger comprises a first microservice which contains a first medical dataset in an encrypted form and which comprises a first access logic to the medical dataset. In the same way, a second record of the ledger comprises a second microservice which contains a second medical dataset in an encrypted form and which comprises a second access logic to the medical dataset. In that way more records of the ledger can be constructed.

A microservice being contained by the ledger can also mean that identification data identifying such microservice are contained, in particular stored, by the ledger. In this case, the compiled microservice is generally stored outside of the ledger and the identification data can be used for using the microservice. In this case, including the further microservice into the ledger generally comprises including the identification data identifying such further microservice into the ledger.

The further medical dataset is different to each medical dataset contained by the microservices which are contained by the ledger before the further microservice is included into the ledger, i.e. the medical dataset is different to the already integrated medical datasets. The further medical dataset can relate to the same patient the already integrated medical datasets relate to. It is also possible that the further medical dataset relates to a different patient than the already integrated medical datasets relate to. The further medical dataset can comprise similar medical data, e.g. medical data acquired by the same medical device, than the already integrated medical datasets. It is also possible that the further medical dataset comprises completely different medical data than the already integrated medical datasets.

The further microservice can be set up according to a method for setting up a microservice according this invention. The further microservice can have a similar or differing architecture than the microservices already contained by the ledger before the further microservice is included into the ledger.

The further microservice is typically included in a further entry of the ledger. Such further entry is typically separated to the entries of the ledger which are already contained by the ledger before the further microservice is included into the ledger. After or by including the further microservice in the ledger, the ledger is updated. In case of a distributed ledger typically all copies of the ledger stored on different nodes of the network are updated.

In typical cases, an already existing ledger containing one or more microservices is enhanced with the further microservice. It is also possible that the further microservice is the first record of the ledger. In that way enhancing the ledger with a further microservice means that the ledger is set up using the further microservice as the first record of the ledger.

The inventors have recognized that by including microservices into a ledger the microservices can be stored a revision-safety way and in a way that they cannot be altered or manipulated. Furthermore, by storing including microservices comprising access logics in a public ledger the medical datasets contained in the microservices can be distributed, while at the same time being accessible only by authorized entities.

According to a further embodiment of the invention the access logic regulates access of an accessing entity to the further medical dataset contained in the further microservice.

According to a further embodiment of the invention the further medical dataset relates to a patient, and the accessing entity is different from the patient.

The inventors have recognized that granting access to an accessing entity being different to the patient the medical data relates to leverages the full potential of the proposed method. For only regulating the access of the patient to its own medical data no microservice-based access logic is necessary, because presumably a patient has access to all medical data relating to him or her.

According to a further embodiment of the invention the further microservice comprises a link to another microservice of the ledger, wherein the link is a hash of the other microservice. In particular, a majority of microservice in the ledger, in particular all microservices except one microservice comprise a link to another microservice of the ledger, wherein the link is a hash of the other microservice.

In particular, the further microservice comprises the link to the other microservice in a way that the record of the ledger, in which the further microservice is included, comprises a hash to the other record of the ledger, in which the other microservice is stored. Each microservice of the ledger can comprise a link to at least one other microservice of the other microservice.

The hash of the other microservice can be calculated using an algorithm which maps information of the other microservice to a hash, i.e. typically a bit string of a fixed size. E.g. the hash of the other microservice can be calculated by hashing a header of the other record of the ledger, in which the other microservice is stored. If only identification data identifying microservices are contained by the ledger, the link typically is a hash of the identification data of the other microservice.

The inventors have recognized that by storing link information or hash values of another microservices in the ledger in the further microservice a manipulation of the another microservice can be prevented, because every manipulation of the another microservice would change the hash of the another microservice, so that the changed hash would be unequal to the hash stored in the further microservice.

According to a further embodiment of the invention the ledger is selected from the group comprising: a blockchain, a tangle, a blocktree, a sidechain. The inventors have recognized that using one ledger from this group allows to use already existing ledgers and to enhance them with microservices. Using already existing ledgers also allows using already existing hardware and software designed for the already existing ledgers, reducing the costs for the implementation of the method.

According to a further embodiment of the invention the step of including the further microservice into the ledger comprises adding a further block to the ledger wherein the further block comprises the further microservice. The inventors have recognized that by using blocks several further microservices can be included into the ledger at the same time, reducing the effort necessary for including a single further microservice into the ledger.

According to a further embodiment of the invention the further microservice comprises an update of a microservice which is contained by a previous block of the ledger, wherein the update of the microservice comprises an updated medical dataset in an encrypted form and/or an updated access logic to the medical dataset. In particular, the further microservice and/or the further block comprising the further microservice comprise an invalidation information, wherein the invalidation information identifies the microservice contained by the previous block of the ledger. The inventors have recognized that by including updated microservices changes within the medical dataset and/or changes to the accessing entity can be implemented into the ledger without changing the microservice contained by the previous block, so that the chain of hashes is kept intact.

According to a further embodiment of the invention the microservices of the ledger are stored in a distributed storage system.

To be stored in a distributed storage system, the microservices of the ledger are typically stored on more than one node of the distributed storage system, in particular in a replicated fashion. Therefore, the ledger can be seen as a distributed ledger. It is, however, also possible that not all microservices of the ledger are stored on a single node of the distributed storage system so that different nodes of the distributed storage system comprise different sets of microservices of the ledger.

The inventors have recognized that by using a distributed storage system the availability of the medical datasets can be assured, even in the case that one or several parts of the distributed storage system fail.

According to a further embodiment of the invention the distributed storage system is a P2P network. The distributed storage system being a P2P network generally means that the distributed storage system has the architecture of a peer-to-peer network (P2P network). Such P2P network typically has interconnected nodes which share resources amongst each other without the use of a centralized administration system.

The inventors have recognized that a P2P network is a distributed storage system with an extraordinary high availability.

According to a further embodiment of the invention the step of providing the further microservice comprises setting up the microservice by a method according to any embodiment. The inventors have recognized that by using a microservice set up with this method incorporates one or several advantages presented for the different aspects and/or embodiments of this method.

The invention relates in one embodiment to a method for accessing a medical dataset contained by a microservice in an encrypted form, wherein the microservice comprises an access logic based on an accessing entity information describing an accessing entity, wherein the access logic defines access conditions to the medical dataset, wherein the method comprises the step of receiving an access request to the medical dataset by a requesting entity, wherein the method furthermore comprises the step of performing a check if the access conditions are met by the requesting entity, and wherein the method furthermore comprises the step of granting access to the medical dataset to the requesting entity depending on the result of the check.

In particular, the step if receiving an access request is executed by an interface, in particular by an interface of an accessing unit. In particular, the step of performing a check is executed by a calculation unit, in particular by a calculation unit of the accessing unit. In particular, the step of granting access to the medical dataset is executed by the calculation unit, in particular by the calculation unit of the accessing unit.

In particular, the step of granting access to the medical dataset to the requesting entity is performed if the result of the check is positive. In particular, the method for accessing a medical dataset can comprise a step of denying access to the medical dataset to the requesting entity if the result of the check is negative. In particular, the step of denying access to the medical dataset is executed by the calculation unit, in particular by the calculation unit of the accessing unit. In particular, the step of granting access to the medical dataset to the requesting entity can comprise the step of providing the medical dataset by the interface, in particular by the interface of the accessing unit, or the step of transmitting the medical dataset from the microservice to the requesting entity by the interface, in particular by the interface of the accessing unit.

In particular the step of performing a check is executed after the step of receiving an access request. In particular, one of the steps of granting access to the medical dataset and of denying access to the medical dataset is executed after the step of performing a check.

The access request is performed by the requesting entity. The access request can typically be performed after the microservice has been set up based on the accessing entity information. In order to receive the access request, the microservice typically provides an access interface comprising access functionality. Such access interface typically accepts request credentials which can be provided by the requesting entity as an input. The request credentials can then be forwarded from the access interface to the access logic which can perform the check if the access conditions are met by the requesting entity. The access interface can be embodied as a webservice so that the access request can e.g. be performed by the requesting entity calling a web address, e.g. a http secure (https) address. After the access request has been received, the microservice can be started and the access logic can check if the access conditions are met by the requesting entity.

The check if the access conditions are met by the requesting entity typically comprises a check if the requesting entity is allowed to access the medical dataset contained by the microservice. The access logic can perform this check based on the request credentials which have been received by the microservice via the access interface.

If the check is positive, i.e. if the requesting entity is an entity entitled to access the medical dataset, the requesting entity is granted access to the medical dataset. If the check is negative, the access logic can deny the requesting entity access to the medical dataset.

The inventors have recognized that by using the described method access to medical dataset contained by the microservice in an encrypted form can be granted in a secure way, in particular so that only an authorized requesting entity can access the medical dataset contained by the microservice.

According to a further embodiment of the invention the medical dataset relates to a patient, and the accessing entity is different from the patient. In particular, the medical dataset also relates to the patient if the medical dataset relates to a group of patients comprising the patient or to a population of patients comprising the patient.

The inventors have recognized that granting access to an accessing entity being different to the patient the medical data relates to leverages the full potential of the proposed method. For only regulating the access of the patient to its own medical data no microservice-based access logic is necessary, because presumably a patient has access to all medical data relating to him or her.

According to a further embodiment of the invention the accessing entity information comprises access credentials, which are stored related to the microservice, wherein the access logic defines the access conditions based on the access credentials, and wherein the result of the check is positive so that access to the medical dataset is granted to the requesting entity if the access credentials are related to request credentials which are related to the requesting entity. In particular the access request comprises the request credentials which are related to the requesting entity.

The request credentials can serve to validate the identity of the requesting entity. The request credentials can be embodied in a similar form than the access credentials. Therefore, the request credentials can be embodied as at least one digital certificate or at least one token or at least one key pair. Other forms of request credentials may also be implemented. The request credentials can be provided to the microservice by the requesting entity as a part of the access request.

The status of entitlement of the requesting entity to access the medical dataset can be determined by checking if the request credentials are related to the access credentials stored in the microservice. For example, if the request credentials are a request certificate, and if the access credentials are an access certificate, the requesting entity can be entitled to access the medical dataset contained by the microservice if the request certificate proves the relation to the access certificate.

The inventors have recognized that using access conditions based on access credentials and request credentials the access request can be checked fast and easily by inspecting the access credentials and the request credentials.

According to a further embodiment of the invention the access credentials are an access certificate and the request credentials are a request certificate, wherein the result of the check is positive so that access to the medical dataset is granted to the requesting entity if the access certificate is related to the request certificate. In particular, the request certificate is belonging to the requesting entity.

The request certificate can be formed in a similar way as the access certificate. Furthermore, the requesting entity typically has access to the private key of the request certificate. Therefore, the request certificate can e.g. also conform to the X.509 standard, i.e. that the request certificate can e.g. be a X.509 certificate. The request certificate can represent the requesting entity as belonging to one of: a representation of persons, a representation of legal entities, a representation of software components, a representation of physical devices.

The inventors have recognized that by using an access certificate and a request certificate, in particular a digital access certificate and a digital request certificate, identities and authorizations of entities can be checked reliably. Furthermore, by using certificates based on an asymmetric encryption system, identities and authorizations can be created and/or verified without relying on shared secrets, which makes it harder to manipulate the process of creating and/or verifying identities and authorizations.

According to a further embodiment of the invention the access certificate belongs to the accessing entity and the access certificate is related to the request certificate if the request certificate is derived from the access certificate. In particular, the microservice can comprise a copy of the access certificate belonging to the accessing entity, and in particular, the microservice does not have access to the private key related the access certificate.

The inventors have recognized that by using an access certificate belonging to the accessing entity during the method step of performing the check no action from the accessing entity is necessary; also for setting up the respective microservice no action from the accessing entity is necessary. In other words, it is possible to set up a microservice without interaction with the accessing entity, which reduces the communication effort and prevents an overload of the accessing entity.

According to a further embodiment of the invention the access certificate belongs to the microservice and is directly authorized by a certificate belonging to the accessing entity and the access certificate is related to the request certificate if the request certificate is derived from the certificate belonging to the accessing entity.

The inventors have recognized that by using an access certificate belonging to the microservice the step of performing the check is independent from the status of the certificate belonging to the accessing entity. In particular, a compromitation or a revocation of the certificate belonging to the microservice not necessarily leads to a compromitation or a revocation of the access certificate.

According to a further embodiment of the invention the access certificate and the request certificate are documented in an access ledger, wherein the access ledger regulates the relations between certificates.

The access ledger generally is built upon certificates, in particular certificates according to the X.509 standard. The access ledger can have a similar structure than the ledger containing the microservices. I.e. the access ledger can also be selected from the group comprising: a blockchain, a tangle, a blocktree, a sidechain. The access ledger generally regulates the relations between the certificates, particularly between the access certificate and the request certificate. The relations between the certificates are typically such that a certificate has an arbitrary number of sub-certificates and at most one parent certificate.

In particular, the access ledger can regulate the relations between the certificates in a way that the access ledger documents the authorization events of certificates in the records of the access ledger. In particular, it can be stored within the access ledger that a first certificate is derived from a second certificate. It is also possible that when one certificate authorizes, in particular signs, another certificate, such authorization can be documented in an event of the access ledger. Therefore, the access ledger can proof the authorization relations between the certificates, in particular between the access certificate and the request certificate. The access ledger can proof if a certificate can indeed by derived from another certificate. It is also possible that the access ledger can document the certificates in a way that the certificates themselves are stored within the access ledger.

The inventors have recognized that using an access ledger the relations between certificates can be stored a revision-safety way and in a way that the relations cannot be altered or manipulated.

According to a further embodiment of the invention the access ledger is selected from the group comprising: a blockchain, a tangle, a blocktree, a sidechain. The inventors have recognized that using an access ledger from this group allows to use already existing ledgers and to enhance them with microservices. Using already existing ledgers also allows using already existing hardware and software designed for the already existing ledgers, reducing the costs for the implementation of the method.

According to a further embodiment of the invention the access request is received by an access interface of the microservice, wherein the access interface is embodied as a webservice. The inventors have recognized that using a webservice access interface improves the accessibility of the microservice, in particular, the access to the microservice can be based on standard methods for accessing a webservice.

According to a further embodiment of the invention the access request and the result of the check are tracked in an access protocol. The inventors have recognized that using an access protocol can be used on the one hand side to limit the number of accesses by the access logic, in particular the number of accesses from a certain accessing or requesting entity, on the other hand an access protocol can be used to identify malicious attacks in the microservice by analyzing the access protocol.

According to a further embodiment of the invention performing the check is based on a further criterion based on at least one item of the following list: an access frequency, an expiration rule of the access conditions, a maximum number of access operations. The inventors have recognized that using such a further criterion can increase the security of the microservice and can be used to prevent brute force or denial-of-service attacks.

According to a further embodiment of the invention the result of the check is positive if the request credentials match the access credentials. In particular, in this case the request credentials and the access credentials are a shared secret (another word is "token"), which is shared between the microservice and the requesting entity. The inventors have recognized that using shared secrets is a simple and efficient way to define access conditions.

According to a further embodiment of the invention the microservice is set up by a method of an embodiment. The inventors have recognized that by using a microservice set up with this method incorporates one or several advantages presented for the different aspects and/or embodiments of this method.

According to a further embodiment of the invention the microservice is included as a further microservice in a ledger by a method according to an embodiment. The inventors have recognized that by using a microservice included as a further microservice in a ledger with this method incorporates one or several advantages presented for the different aspects and/or embodiments of this method.

The invention relates in one embodiment to a method for accessing information stored in a digital twin, wherein the digital twin comprises information about a real-world source, wherein a profile is assigned to the digital twin and wherein the profile defines access to a subset of the information stored in the digital twin, wherein the profile is configurable by the real-world source, wherein the method comprises the step of receiving an access request to the subset of information stored in the digital twin by a requesting entity, wherein the method furthermore comprises the step of performing a check if the requesting entity is subject to the profile, and wherein the method furthermore comprises the step of granting access to the subset of information stored in the digital twin depending on the result of the check.

In particular, the step if receiving an access request is executed by an interface, in particular by an interface of an digital twin accessing unit. In particular, the step of performing a check is executed by a calculation unit, in particular by a calculation unit of the digital twin accessing unit. In particular, the step of granting access to the subset of information is executed by the calculation unit, in particular by the calculation unit of the digital twin accessing unit.

In particular, the step of granting access to the subset of information to the requesting entity is performed if the result of the check is positive. In particular, the method for accessing information stored in a digital twin can comprise a step of denying access to the subset of information to the requesting entity if the result of the check is negative. In particular, the step of denying access to the subset of information is executed by the calculation unit, in particular by the calculation unit of the digital twin accessing unit. In particular, the step of granting access to the medical dataset to the requesting entity can comprise the step of providing the subset of information by the interface, in particular by the interface of the digital twin accessing unit, or the step of transmitting the medical dataset from the digital twin to the requesting entity by the interface, in particular by the interface of the digital twin accessing unit.

In particular the step of performing a check is executed after the step of receiving an access request. In particular, one of the steps of granting access to the subset of information and of denying access to the subset of information is executed after the step of performing a check.

Generally, the digital twin is the digital representation of the real-world source. The digital twin directly assigned to the real-world source after the digital twin is created. Typically, the digital twin cannot be detached from the real-world source afterwards. Therefore, each digital twin is typically unique and cannot be multiplied or forked. The digital twin typically comprises a data storage module in which the information about the real-world source is stored. The digital twin also typically comprises an information interface which can be used to receive new information. Furthermore, the digital twin typically comprises an access interface which can receive access requests to subsets of information stored in the digital twin.

The real-world source typically is a person. In particular cases, the real-world source is a patient. It is also possible that the real-world source is an object, an animal, a group of persons or a legal entity. Typically, only one digital twin is assigned the one single real-world source.

The information stored in the digital twin relates to the real-world source. The information typically originates from sensor data related to the real-world source. The information can continuously be updated and/or enhanced. Multiple sources can be used as a basis to generate the information. To provide some examples, the sensor data can be based on photo or video sensors, GPS sensors, physiological sensors, etc. The information can also comprise medical datasets. The information is typically stored in the digital twin in an encrypted form. Information can also originate from a transfer of information from another digital twin. In this case, the data received from the other digital twin can be marked as such, e.g. marked that they stem from another real-world source.

Typically, metadata is assigned to the information stored in the digital twin. Such metadata can e.g. comprise one or more items of the following list: a timestamp when the information was generated, a location where the information was generated, the real-world source which is the subject or the information, the real-world source which created the information, the owner of the information (typically by default the real-world source).

Generally, the profile can be seen as the controlled representation of the digital twin in the digital world. The profile is directly linked to the digital twin. Information stored in the digital twin can be shared with the digital world via the profile. Typically, the profile does not store or carry information from the digital twin, but rather regulates the access to the information stored in the digital twin. The digital twin can communicate with the digital world, e.g. with a profile of another digital twin, using the profile. The profiles can be set up in a hierarchical way so that one profile can comprise one or more sub-profiles. In contrast to the digital twin, profiles can typically be copied, multiplied or reassigned.

The profile generally contains rules of entitlement based on which the information stored in the digital twin can be accessed.

By configuring the profile, the real-world source can control which information stored in the digital twin can be shared via the profile. Furthermore, conditions under which the subset of information is shared with the requesting entity can be configured by the real-world source. Therefore, the digital twin typically comprises a profile interface which can be used to configure the profile assigned to the digital twin, e.g. to configure information sharing rules or to set up a new profile or to delete an existing profile.

The configuration of the profile can comprise the configuration of rules of entitlement to access information stored in the digital twin by the real-world source. Such configuration of the rules can comprise a free design of the rules from scratch. It is also possible that a given rule, e.g. stored in a rule library, is set by the real-world source. It is also possible that a template profile comprising a set of rules is used as a configurable basis for the profile. Therefore, the profile can be derived from a template profile. The template profile can be loaded from a template profile library.

The requesting entity is typically different to the real-world source. The reason for this is that the real-world source typically has automatic access to all information stored in the digital twin. Therefore, typically no check if the real-world source is subject to the profile is necessary to determine if the real-world source can access the information stored in the digital twin.

The digital twin typically comprises an access interface which can receive the access request to the subset of information stored in the digital twin. Therefore, the requesting entity can use the access interface of the digital twin to issue the access request. Then, the access request is typically passed from the access interface to an access logic of the digital twin which can perform the check if the requesting entity is entitled to access the subset of information.

Using the check if the requesting entity is subject to the profile, it can be determined if the requesting entity is entitled to access the subset of information stored in the digital twin. If the requesting entity is subject to the profile, the requesting entity can be entitled to access the subset of information. If the requesting entity is not subject to the profile, the requesting entity can be denied access to the subset of information. The check can be performed by the access logic of the digital twin.

The check if the requesting entity is subject to the profile may comprise a check if the requesting entity conforms to the rules of entitlement based on which the information stored in the digital twin can be accessed according to the profile. E.g. the profile can regulate that only a certain entity, e.g. a group of people, may access the subset of information stored in the digital twin. Performing the check can then comprise a check if the requesting entity belongs to the certain entity or is the certain entity.

If the result of the check is that the requesting entity is subject to the profile, the requesting entity can access the subset of information stored on the digital twin. Therefore, the digital twin typically comprises an output interface which enables access to the subset of information stored in the digital twin. This output interface is typically coupled to the access logic which performs the check if the requesting entity is entitled to access the subset of information. Access to the subset of information typically comprises viewing the content of the subset of information. Access to the subset of information can also comprise downloading or modifying the subset of information.

The inventors have recognized that by using the described method access to information stored in a digital twin can be granted in a secure way, in particular so that only an authorized requesting entity can access the information stored in a digital twin.

According to a further embodiment of the invention the requesting entity is different from the real-world source. The inventors recognized that the real-world source typically has automatic access to all information stored in the digital twin. Therefore, typically no check if the real-world source is subject to the profile is necessary to determine if the real-world source can access the information stored in the digital twin.

According to a further embodiment of the invention a further digital twin comprises information about the requesting entity and a further profile, which is configurable by the requesting entity, is assigned to the further digital twin, wherein the access request is performed by the further profile of the further digital twin.

The further digital twin is assigned to the requesting entity. Therefore, the requesting entity can manage the further profile assigned to the further digital twin.

The further profile of the further digital twin issues the access request. Therefore, the further profile does not only contain functionality to regulate access to the information about the requesting entity, but also contains an issuing functionality to issue the access request. Therefore, the digital twins can communicate with one another using the profiles assigned to the digital twins.

The inventors have recognized that using a further digital twin comprising information about the requesting entity the exchange of information between digital twins can be executed automatically based on the profiles of the digital twin and the further profile of the further digital twin.

According to a further embodiment of the invention the digital twin comprises multiple microservices, wherein the information is contained by the multiple microservices in an encrypted form and the subset of the information is contained by a subset of the multiple microservices.

The digital twin comprising multiple microservices generally means that the digital twin is implemented in a way that the information stored in the digital twin is stored distributed over the multiple microservices. I.e. a first microservice of the multiple microservices contains a first part of the information stored in the digital twin and a second microservice of the multiple microservices contains a second part of the information stored in the digital twin. Once additional information is added to the digital twin, an additional microservice containing the additional information can be set up and added to the multiple microservices.

The multiple microservices comprise a storage functionality which can contain the information in an encrypted form. Therefore, the multiple microservices can also contain encryption functionality. The multiple microservices typically contain access logics to access the information stored in the multiple microservices. The access logics can define access conditions to the information stored in the multiple microservices and the access logics are typically configured to grant access to the information if the access conditions are fulfilled.

The subset of the information is typically contained by one or more microservices which collectively form the subset of the multiple microservices. The subset of information can in some cases also be the complete information stored in the digital twin. The profile is typically related to the subset of microservices so that the profile defines the access conditions to the subset of microservices. A requesting entity, which has access to the subset of information, typically must also have access to all microservices of the subset of microservices.

The inventors have recognized that by using multiple microservices to store the information presented advantages of using microservices can also be obtained with this method.

According to a further embodiment of the invention the multiple microservices comprise access logics to the information contained by the multiple microservices, wherein the profile defines that the access logics of the subset of the multiple microservices grant access to the subset of information to the requesting entity if the requesting entity is subject to the profile. The inventors have recognized that by this setup access to different parts of information stored in the digital twin can be granted using the access logics of the multiple microservices.

According to a further embodiment of the invention the access logics of the subset of the multiple microservices are based on accessing entity information describing the same accessing entity. The inventors have recognized that by using accessing entity information describing the same accessing entity the access to this accessing entity can be defined in a simple and efficient way.

According to a further embodiment of the invention the information is medical data and the multiple microservices are set up by a method according to any embodiment. The inventors have recognized that using a microservice set up by the method incorporates one or several advantages presented for the different aspects and/or embodiments of this method.

According to a further embodiment of the invention the information is medical data and the multiple microservices are included as further microservices in a ledger by a method according to any embodiment. The inventors have recognized that using a microservice included as further microservice in a ledger by the method incorporates one or several advantages presented for the different aspects and/or embodiments of this method.

According to a further embodiment of the invention the information is medical data and access to the subset of information is granted by a method according to any embodiment. The inventors have recognized that using the access granting method incorporates one or several advantages presented for the different aspects and/or embodiments of this method.

According to a further embodiment of the invention performing a check if the requesting entity is subject to the profile comprises checking the validity of three matching conditions and the access is granted to the subset of information if at least two of the three matching conditions are met, wherein the three matching conditions are a purpose matching condition, a trust level matching condition and an assignment matching condition.

The check can be performed if the access request of the requesting entity fulfills two or three of the listed three matching conditions. The purpose matching condition particularly relates to the purpose why the requesting entity wants to get access to the subset of information. The purpose matching conditions typically is situation specific and has only temporally limited validity. The purpose matching condition is generally fulfilled if the purpose of the access request can be validated, e.g. because of situation circumstances or because of general rules set by the real-world source. The trust level matching condition particularly refers to a property of the requesting entity, namely particularly a trust level of the requesting entity. The trust level matching condition is generally fulfilled if the requesting entity has a high enough trust level, e.g. over a threshold defined by the real-world source. The assignment matching condition typically refers to an assignment of the real-world source that the requesting entity should be granted access to the subset of information. Such assignment can be valid generally for a requesting entity or can be limited to certain circumstances or a certain situation. The assignment matching condition is generally fulfilled if a specific assignment is issued by the real-world source that the requesting entity should be granted access to the subset of information.

The inventors have recognized that by using this two out of three approach access to the subset of information can also be granted in exceptional situation, for example in emergency situations.

According to a further embodiment of the invention the profile is derived from a template profile. In particular, a template profile can be another profile from the digital twin or another profile from another digital twin. The inventors have recognized that deriving profiles from template profiles simplifies and expedites the definition process of profiles.

According to a further embodiment of the invention multiple profiles defining access to different subsets of information are assigned to the digital twin.

A first profile of the multiple profiles can regulate the access to a first subset of information and a second profile of the multiple profiles can regulate the access to a second subset of information. If a requesting entity requests access to a specific subset of information, the check can be performed if the requesting entity is subject to the corresponding profile. If a requesting entity requests general access to information stored in the digital twin, it can be checked which profiles of the multiple profiles the requesting entity is subject to. Accordingly, the requesting entity can be granted access to the corresponding subsets of information. It is also possible that the multiple profiles of the same digital twin communicate with another.

The inventors have recognized that by using multiple profiles access to the different subsets of information contained in the microservice can be granted to different accessing entities, so it is not necessary to have different digital twins for the same subset of information. So the memory needed for storing digital twins can be reduced. Furthermore it is not necessary to update digital twins.

According to a further embodiment of the information comprised by the digital twin is stored in a distributed storage system. The inventors have recognized that by using a distributed storage system the availability of information comprised by the digital twin can be assured, even in the case that one or several parts of the distributed storage system fail.

According to a further embodiment of the invention the distributed storage system is a P2P network. The inventors have recognized that a P2P network is a distributed storage system with an extraordinary high availability.

The invention relates in one embodiment to a setting up unit for setting up a microservice, comprising the following units:

interface, configured for receiving a medical dataset, furthermore configured for receiving accessing entity information describing an accessing entity, calculation unit, configured for setting up the microservice based on the accessing entity information, wherein the microservice contains the medical dataset in an encrypted form, wherein the microservice comprises an access logic based on the accessing entity information and wherein the access logic defines access conditions to the medical dataset and is configured to grant access to the medical dataset if the access conditions are fulfilled.

In particular the setting up unit can be configured to execute the method for setting up a microservice according to the invention and its aspects and/or embodiments. The setting up unit is configured to execute the method its aspects and/or embodiments by the interface and the calculation unit being configured to execute the respective method steps.

The invention relates in one embodiment to a medical apparatus comprising a setting up unit. In particular, a medical apparatus may be a magnetic resonance tomography apparatus, an X-Ray apparatus, a computed tomography apparatus, an angiography apparatus, a C-Arm X-Ray apparatus, an ultrasound apparatus, a laboratory diagnostic apparatus, or a measurement apparatus measuring vital values of a certain patient.

The invention relates in one embodiment to a computer program product comprising a computer program, the computer program being loadable into a memory unit of a setting up unit, including program code sections to make the setting up unit execute the method for setting up a microservice according to an embodiment of the invention when the computer program is executed in the setting up unit.

The invention relates in one embodiment to a computer-readable medium, on which program code sections of a computer program are saved, the program code sections being loadable into and/or executable in a setting up unit to make the setting up unit execute the method for setting up a microservice according to an embodiment of the invention when the program code sections are executed in the setting up unit.

The invention relates in one embodiment to an enhancing unit for enhancing a ledger with a further microservice, comprising the following units:

interface configured for receiving the ledger, wherein the ledger contains microservices, wherein each of the microservices contains a medical dataset in an encrypted form and comprises an access logic to the medical dataset, furthermore configured for receiving a further medical dataset, calculation unit configured for providing the further microservice containing the further medical dataset in an encrypted form and comprising an access logic to the further medical dataset, furthermore configured for including the further microservice into the ledger.

In particular the enhancing unit can be configured to execute the method for enhancing a ledger with a further microservice according to the invention and its aspects and/or embodiments. The enhancing unit is configured to execute the method its aspects and/or embodiments by the interface and the calculation unit being configured to execute the respective method steps.

The invention relates in one embodiment to a medical apparatus comprising a enhancing unit.

The invention relates in one embodiment to a computer program product comprising a computer program, the computer program being loadable into a memory unit of a enhancing unit, including program code sections to make the enhancing unit execute the method for enhancing a ledger with a further microservice according to an embodiment of the invention when the computer program is executed in the enhancing unit.

The invention relates in one embodiment to a computer-readable medium, on which program code sections of a computer program are saved, the program code sections being loadable into and/or executable in an enhancing unit to make the enhancing unit execute the method for enhancing a ledger with a further microservice according to an embodiment of the invention when the program code sections are executed in the enhancing unit.

The invention relates in one embodiment to an accessing unit for accessing a medical dataset contained by a microservice in an encrypted form, wherein the microservice comprises an access logic based on an accessing entity information describing an accessing entity, wherein the access logic defines access conditions to the medical dataset, wherein the accessing unit comprises the following units:

interface, configured for receiving an access request to the medical dataset by a requesting entity, calculation unit, configured for performing a check if the access conditions are met by the requesting entity, furthermore configured for granting access to the medical dataset to the requesting entity depending on the result of the check.

In particular the accessing unit can be configured to execute the method for accessing a medical dataset contained by a microservice in an encrypted form according to the invention and its aspects and/or embodiments. The accessing unit is configured to execute the method its aspects and/or embodiments by the interface and the calculation unit being configured to execute the respective method steps.

The invention relates in one embodiment to a computer program product comprising a computer program, the computer program being loadable into a memory unit of an accessing unit, including program code sections to make the accessing unit execute the method for accessing a medical dataset contained by a microservice in an encrypted form according to an embodiment of the invention when the computer program is executed in the accessing unit.

The invention relates in one embodiment to a computer-readable medium, on which program code sections of a computer program are saved, the program code sections being loadable into and/or executable in an accessing unit to make the accessing unit execute the method for accessing a medical dataset contained by a microservice in an encrypted form according to an embodiment of the invention when the program code sections are executed in the accessing unit.

The invention relates in one embodiment to a digital twin accessing unit for accessing information stored in a digital twin, wherein the digital twin comprises information about a real-world source, wherein a profile is assigned to the digital twin and wherein the profile defines access to a subset of the information stored in the digital twin, wherein the profile is configurable by the real-world source, wherein the accessing unit comprises the following units:

interface, configured for receiving an access request to the subset of information stored in the digital twin by a requesting entity, calculation unit, configured for performing a check if the requesting entity is subject to the profile, furthermore configured for granting access to the subset of information stored in the digital twin depending on the result of the check.

In particular the digital twin accessing unit can be configured to execute the method for accessing information stored in a digital twin according to the invention and its aspects and/or embodiments. The digital twin accessing unit is configured to execute the method its aspects and/or embodiments by the interface and the calculation unit being configured to execute the respective method steps.

The invention relates in one embodiment to a computer program product comprising a computer program, the computer program being loadable into a memory unit of a digital twin accessing unit, including program code sections to make the digital accessing unit execute the method for accessing information stored in a digital twin according to an embodiment of the invention when the computer program is executed in the digital twin accessing unit.

The invention relates in one embodiment to a computer-readable medium, on which program code sections of a computer program are saved, the program code sections being loadable into and/or executable in a digital twin accessing unit to make the digital twin accessing unit execute the method for accessing information stored in a digital twin according to an embodiment of the invention when the program code sections are executed in the digital twin accessing unit.

The realization of the invention or one of its aspects and/or embodiments by a computer program product and/or a computer-readable medium has the advantage that already existing setting up units, enhancing units, accessing units and/or digital twin accessing units can be easily adopted by software updates in order to work as proposed by the invention.

The the computer program products can be, for example, a computer program or comprise another element apart from the computer program. This other element can be hardware, for example a memory device, on which the computer program is stored, a hardware key for using the computer program and the like, and/or software, for example a documentation or a software key for using the computer program.

Further embodiments of the invention are as follows:

Embodiment 1

A method for setting up a microservice, comprising the following steps:
receiving a medical dataset,
receiving accessing entity information describing an accessing entity,
setting up the microservice based on the accessing entity information,
wherein the microservice contains the medical dataset in an encrypted form,
wherein the microservice comprises an access logic based on the accessing entity information, and
wherein the access logic defines access conditions to the medical dataset and is configured to grant access to the medical dataset if the access conditions are fulfilled.

Embodiment 2

The method according to embodiment 1, wherein the medical dataset relates to a patient, and wherein the accessing entity is different from the patient.

Embodiment 3

The method according to embodiment 1 or 2, wherein the accessing entity information comprises access credentials, which are stored related to the microservice, wherein the access logic defines the access conditions based on the access credentials, and wherein the access conditions are fulfilled if the access credentials are related to a requesting entity which requests access to the medical dataset.

Embodiment 4

The method according to embodiment 3, wherein the access credentials are an access certificate and the access conditions are fulfilled if the access certificate is related to the requesting entity.

Embodiment 5

The method according to embodiment 4, wherein the access certificate is an X.509 certificate.

Embodiment 6

The method according to any of the embodiments 4 or 5, wherein the access certificate belongs to the accessing entity and the access certificate is related to the requesting entity if the identity of the requesting entity is verified by the access certificate.

Embodiment 7

The method according to any of the embodiments 4 or 5, wherein the access certificate belongs to the microservice and is derived from a certificate belonging to the accessing entity, and wherein the access certificate is related to the requesting entity if the identity of the requesting entity is verified by the certificate belonging to the accessing entity.

Embodiment 8

The method according to any of the preceding embodiments, wherein the microservice comprises multiple access logics based on different accessing entity informations and defining different access conditions to the medical dataset.

Embodiment 9

The method according to embodiment 8, wherein the medical dataset relates to a patient, wherein a first of the different accessing entity informations relates to an accessing entity being different from the patient, and wherein a second of the different accessing entity informations relates to the patient.

Embodiment 10

The method according to any of the preceding embodiments, wherein receiving the medical dataset comprises:
receiving encryption information,
encrypting the medical dataset using asymmetric encryption based on the encryption information.

Embodiment 11

The method according to any of the embodiments 1 to 9, wherein setting up the microservice comprises
receiving encryption information,
encrypting the medical dataset using asymmetric encryption based on the encryption information.

Embodiment 12

A method for enhancing a ledger with a further microservice, comprising the following steps:
receiving the ledger, wherein the ledger contains microservices, wherein each of the microservices contains a medical dataset in an encrypted form and comprises an access logic to the medical dataset,
receiving a further medical dataset,
providing the further microservice containing the further medical dataset in an encrypted form and comprising an access logic to the further medical dataset,
including the further microservice into the ledger.

Embodiment 13

The method according to embodiment 10, wherein the access logic of the further microservice regulates access of an accessing entity to the further medical dataset contained in the further microservice.

Embodiment 14

The method according to embodiment 13, wherein the further medical dataset relates to a patient, and wherein the accessing entity is different from the patient.

Embodiment 15

The method according to any of the embodiments 12 to 14, wherein the further microservice comprises a link to another microservice of the ledger wherein the link is a hash of the other microservice.

Embodiment 16

The method according to any of the embodiment 12 to 15, wherein the ledger is selected from the group comprising: a blockchain, a tangle, a blocktree, a sidechain.

Embodiment 17

The method according to embodiment 12, wherein including the further microservice into the ledger comprises adding a further block to the ledger wherein the further block comprises the further microservice.

Embodiment 18

The method according to embodiment 17, wherein the further microservice comprises an update of a microservice which is contained by a previous block of the ledger, wherein the update of the microservice comprises an updated medical dataset in an encrypted form and/or an updated access logic to the medical dataset.

Embodiment 19

The method according to any of the embodiments 12 to 18, wherein the microservices of the ledger are stored in a distributed storage system.

Embodiment 20

The method according to embodiment 19, wherein the distributed storage system is a P2P network.

Embodiment 21

The method according to any of the embodiments 12 to 20, wherein providing the further microservice comprises setting up the microservice by a method according to any of the embodiments 1 to 11.

Embodiment 22

A method for accessing a medical dataset contained by a microservice in an encrypted form, wherein the microservice comprises an access logic based on an accessing entity information describing an accessing entity, wherein the access logic defines access conditions to the medical dataset, wherein the method comprises the following steps:
receiving an access request to the medical dataset by a requesting entity,
performing a check if the access conditions are met by the requesting entity,
granting access to the medical dataset to the requesting entity depending on the result of the check.

Embodiment 23

The method according to embodiment 22 wherein the medical dataset relates to a patient, and wherein the accessing entity is different from the patient.

Embodiment 24

The method according to any of the embodiments 22 or 23, wherein the accessing entity information comprises access credentials, which are stored related to the microservice, wherein the access logic defines the access conditions based on the access credentials and wherein the result of the check is positive so that access to the medical dataset is granted to the requesting entity if the access credentials are related to request credentials which are related to the requesting entity.

Embodiment 25

The method according to embodiment 24, wherein the access credentials are an access certificate and the request credentials are a request certificate, wherein the result of the check is positive so that access to the medical dataset is granted to the requesting entity if the access certificate is related to the request certificate.

Embodiment 26

The method according to embodiment 25, wherein the access certificate belongs to the accessing entity and the access certificate is related to the request certificate if the request certificate is derived from the access certificate.

Embodiment 27

The method according to embodiment 25, wherein the access certificate belongs to the microservice and is directly authorized by a certificate belonging to the accessing entity and the access certificate is related to the request certificate if the request certificate is derived from the certificate belonging to the accessing entity.

Embodiment 28

The method according to any of the embodiments 25 to 27, wherein the access certificate and the request certificate are documented in an access ledger and wherein the access ledger regulates the relations between certificates.

Embodiment 29

The method according to embodiment 28, wherein the access ledger is selected from the group comprising: a blockchain, a tangle, a blocktree, a sidechain.

Embodiment 30

The method according to any of the embodiments 22 to 29, wherein the access request is received by an access interface of the microservice, wherein the access interface is embodied as a webservice.

Embodiment 31

The method according to any of the embodiments 22 to 30, wherein the access request and the result of the check are tracked in an access protocol.

Embodiment 32

The method according to any of the embodiments 22 to 31, wherein performing the check is based on a further criterion based on at least one item of the following list: an access frequency, an expiration rule of the access conditions, a maximum number of access operations.

Embodiment 33

The method according to embodiment 22, wherein the result of the check is positive if the request credentials match the access credentials.

Embodiment 34

The method according to any of the embodiments 22 to 33, wherein the microservice is set up by a method according to any of the embodiments 1 to 11.

Embodiment 35

The method according to any of the embodiments 22 to 33, wherein the microservice is included as a further microservice in a ledger by a method according to any of the embodiments 12 to 21.

Embodiment 36

A method for accessing information stored in a digital twin, wherein the digital twin comprises information about a real-world source, wherein a profile is assigned to the digital twin and wherein the profile defines access to a subset of the information stored in the digital twin, wherein the profile is configurable by the real-world source, wherein the method comprises the following steps:
receiving an access request to the subset of information stored in the digital twin by a requesting entity,
performing a check if the requesting entity is subject to the profile,
granting access to the subset of information stored in the digital twin depending on the result of the check.

Embodiment 37

The method according to Embodiment 36, wherein the requesting entity is different from the real-world source.

Embodiment 38

The method according to any of the embodiments 36 or 37, wherein a further digital twin comprises information about the requesting entity and a further profile, which is configurable by the requesting entity, is assigned to the further digital twin, wherein the access request is received by the further profile of the further digital twin.

Embodiment 39

The method according to any of the embodiments 36 to 38, wherein the digital twin comprises multiple microservices wherein the information is contained by the multiple microservices in an encrypted form and the subset of the information is contained by a subset of the multiple microservices.

Embodiment 40

The method according to embodiment 39, wherein the multiple microservices comprise access logics to the information contained by the multiple microservices, wherein the profile defines that the access logics of the subset of the multiple microservices grant access to the subset of information to the requesting entity if the requesting entity is subject to the profile.

Embodiment 41

The method according to embodiment 40, wherein the access logics of the subset of the multiple microservices are based on accessing entity information describing the same accessing entity.

Embodiment 42

The method according to any of the embodiments 39 to 41, wherein the information is medical data and the multiple microservices are set up by a method according to any of the embodiments 1 to 11.

Embodiment 43

The method according to any of the embodiments 39 to 42, wherein the information is medical data and the multiple microservices are included as further microservices in a ledger by a method according to any of the embodiments 12 to 21.

Embodiment 44

The method according to any of the embodiments 39 to 43, wherein the information is medical data and access to the subset of information is granted by a method according to any of the embodiments 22 to 35.

Embodiment 45

The method according to any of the embodiments 39 to 44, wherein performing a check if the requesting entity is subject to the profile comprises checking the validity of three matching conditions and the access is granted to the subset of information if at least two of the three matching conditions are met, wherein the three matching conditions are a purpose matching condition, a trust level matching condition and an assignment matching condition.

Embodiment 46

The method according to any of the embodiments 39 to 45, wherein the profile is derived from a template profile.

Embodiment 47

The method according to any of the embodiments 39 to 46, wherein multiple profiles defining access to different subsets of information are assigned to the digital twin.

Embodiment 48

The method according to any of the embodiments 39 to 46, wherein the information comprised by the digital twin is stored in a distributed storage system.

Embodiment 49

The method according to embodiment 48, wherein the distributed storage system is a P2P network.

Embodiment 50

A setting up unit for setting up a microservice, comprising the following units:
an interface, configured for receiving a medical dataset, furthermore configured for receiving accessing entity information describing an accessing entity,
a calculation unit, configured for setting up the microservice based on the accessing entity information, wherein the microservice contains the medical dataset in an encrypted form, wherein the microservice comprises an access logic based on the accessing entity information and wherein the access logic defines access conditions to the medical dataset and is configured to grant access to the medical dataset if the access conditions are fulfilled.

Embodiment 51

The setting up unit according to embodiment 50, furthermore configured to execute the method according to one of the embodiments 2 to 11.

Embodiment 52

A medical apparatus comprising the setting up unit according to embodiment 50 or 51.

Embodiment 53

A computer program product comprising a computer program, the computer program being loadable into a memory unit of a setting up unit, including program code sections to make the setting up unit execute the method of any one of embodiments 1 to 11 when the computer program is executed in the setting up unit.

Embodiment 54

A computer-readable medium, on which program code sections of a computer program are saved, the program code sections being loadable into and/or executable in a setting up unit to make the setting up unit execute the method of any one of the embodiments 1 to 11 when the program code sections are executed in the setting up unit.

Embodiment 55

An enhancing unit for enhancing a ledger with a further microservice, comprising the following units:
an interface configured for receiving the ledger, wherein the ledger contains microservices, wherein each of the microservices contains a medical dataset in an encrypted form and comprises an access logic to the medical dataset, furthermore configured for receiving a further medical dataset,
a calculation unit configured for providing the further microservice containing the further medical dataset in an encrypted form and comprising an access logic to the further medical dataset,
furthermore configured for including the further microservice into the ledger.

Embodiment 56

The enhancing unit according to embodiment 55, furthermore configured to execute the method according to one of the embodiments 13 to 21.

Embodiment 57

A medical apparatus comprising the enhancing unit according to embodiment 55 or 56.

Embodiment 58

A computer program product comprising a computer program, the computer program being loadable into a memory unit of an enhancing unit, including program code sections to make the enhancing unit execute the method of any one of embodiments 12 to 21 when the computer program is executed in the enhancing unit.

Embodiment 59

A computer-readable medium, on which program code sections of a computer program are saved, the program code sections being loadable into and/or executable in an enhancing unit to make the enhancing unit execute the method of any one of the embodiments 12 to 21 when the program code sections are executed in the enhancing unit.

Embodiment 60

An accessing unit for accessing a medical dataset contained by a microservice in an encrypted form, wherein the microservice comprises an access logic based on an accessing entity information describing an accessing entity, wherein the access logic defines access conditions to the medical dataset, wherein the accessing unit comprises the following units:
an interface, configured for receiving an access request to the medical dataset by a requesting entity,
a calculation unit, configured for performing a check if the access conditions are met by the requesting entity, furthermore configured for granting access to the medical dataset to the requesting entity depending on the result of the check.

Embodiment 61

The accessing unit according to embodiment 60, furthermore configured to execute the method according to one of the embodiments 23 to 35.

Embodiment 62

A computer program product comprising a computer program, the computer program being loadable into a memory unit of an accessing unit, including program code sections to make the accessing unit execute the method of any one of embodiments 22 to 35 when the computer program is executed in the accessing unit.

Embodiment 63

A computer-readable medium, on which program code sections of a computer program are saved, the program code sections being loadable into and/or executable in an accessing unit to make the accessing unit execute the method of any one of the embodiments 22 to 35 when the program code sections are executed in the accessing unit.

Embodiment 64

A digital twin accessing unit for accessing information stored in a digital twin, wherein the digital twin comprises information about a real-world source, wherein a profile is assigned to the digital twin and wherein the profile defines access to a subset of the information stored in the digital twin, wherein the profile is configurable by the real-world source, wherein the digital twin accessing unit comprises the following units:

an interface, configured for receiving an access request to the subset of information stored in the digital twin by a requesting entity, a calculation unit, configured for performing a check if the requesting entity is subject to the profile, furthermore configured for granting access to the subset of information stored in the digital twin depending on the result of the check.

Embodiment 65

The digital twin accessing unit according to embodiment 64, furthermore configured to execute the method according to one of the embodiments 37 to 49.

Embodiment 66

A computer program product comprising a computer program, the computer program being loadable into a memory unit of a digital twin accessing unit, including program code sections to make the digital twin accessing unit execute the method of any one of embodiments 36 to 49 when the computer program is executed in the digital twin accessing unit.

Embodiment 67

A computer-readable medium, on which program code sections of a computer program are saved, the program code sections being loadable into and/or executable in a digital twin accessing unit to make the digital twin accessing unit execute the method of any one of the embodiments 36 to 49 when the program code sections are executed in the digital twin accessing unit.

The properties, features and advantages of this invention described above, as well as the manner they are achieved, become clearer and more understandable in the light of the following description and embodiments, which will be described in details in the context of the drawings and of pseudocode. This following description does not limit the invention on the contained embodiments. Same components or parts can be labeled with the same reference signs in different figures. In general the figures are not for scale.

Within the pseudocode each microservice MS is an instance of a class in an object oriented programming model. This example and/or the following pseudocode is only for illustrator purpose and is not to be understand to limit the scope of the word microservice. For example, a microservice MS can also be or comprise a process running in a (virtual) operating system, a container (e.g. a Docker container), a webservice, an application programming interface (short "API") or suchlike. Furthermore, the pseudocode is not to be understood as real programming code or as a restriction to a certain implementation, but as a template or suggestion for an actual implementation in an arbitrary programming language.

FIG. 1 displays a schematic view of a patient PAT sharing datasets to multiple entities. In this example, for a patient PAT there are two physicians PHY.1, PHY.2 that should be able to access all of the medical data DAT.1, DAT.2 that is related to the patient PAT (in this case, there is a first dataset DAT.1 and a second dataset DAT.2). Furthermore, some entity ENT.1 (for example all emergency physicians) should have access to a certain subset of medical data (here the second dataset DAT.2) related to the patient (for example, the emergency physicians should have access only to laboratory data of the patient PAT, but not on psychological reports related to the patient PAT). For the entity ENT.1 with access to this second dataset DAT.2, there might be one or more levels of subentities ENT.2 (in this example the emergency department of a certain hospital), and associated entities which perform the actual request for the second dataset DAT.2, in this case the two emergency physicians PHY.3, PHY.4 of the emergency department of the certain hospital.

In the displayed example, the patient PAT may have some information PAT.INF which identifies the patient. This information might be some identifying information naturally connected to the patient (e.g. his fingerprint or his DNA), or it might be some synthetic identifying information, (e.g. a passport, a digital passphrase or a digital certificate). Also the entities ENT.1, ENT.2 have such identifying information ENT.1.INF, ENT.2.INF. The identifying information may be constructed using an external authority CA (e.g. a certificate authority), which uses some own identifying information CA.INF for verifying the identifying information of the other entities PAT, ENT.1, ENT.2.

To grant access to all or some of its datasets, consent of the patient that certain entities ENT.1, ENT.2 or physicians PHY.1, PHY.2 are allowed to access certain datasets has to be documented and stored. In the displayed example, the physicians PHY.1, PHY.2 which are able to access all of the patient's PAT datasets DAT.1, DAT.2 have some information PAT.INF.PHY.1, PAT.INF.PHY.2 which logs the consent of the patient PAT to access all of its datasets DAT.1, DAT.2. Furthermore, the data DAT.1, DAT.2 related to the patient PAT has some information PAT.INF.DAT.1, PAT.INF.DAT.2 that identifies the datasets DAT.1, DAT.2 as originating from the patient PAT. By comparing the information PAT.INF.PHY.1, PAT.INF.PHY.2 of the physicians PHY.1, PHY.2 and the information PAT.INF.DAT.1, PAT.INF.DAT.2 of the datasets DAT.1, DAT.2 access of the physicians PHY.1, PHY.2 to the datasets DAT.1, DAT.2 can be regulated.

Furthermore the two physicians PHY.3, PHY.4 employed by the emergency department of the hospital must have information ENT.2.INF.PHY.3, ENT.2.INF.PHY.4 about their employment (e.g. an ID card of the hospital, or a digital certificate issued by the hospital). In order to grant access to the second dataset DAT.2 to the physicians PHY.3, PHY.4, their information ENT.2.INF.PHY.3, ENT.2.INF.PHY.4 has to be compared with another set of information ENT.1.INF.DAT.2 contained in the second dataset DAT.2, so that access to the second dataset DAT.2 will be granted for all physicians PHY.3, PHY.4 belonging to the entity ENT.1 or any sub-entity ENT.2 of the entity ENT.1.

In contrast to the second dataset DAT.2, the first dataset DAT.1 does not contain information from the entity ENT.1, so the physicians PHY.3, PHY.4 are not allowed to access the first dataset DAT.1.

In the following, methods and apparatuses are described to realize the described selective access to medical datasets of patients.

Figure 3:
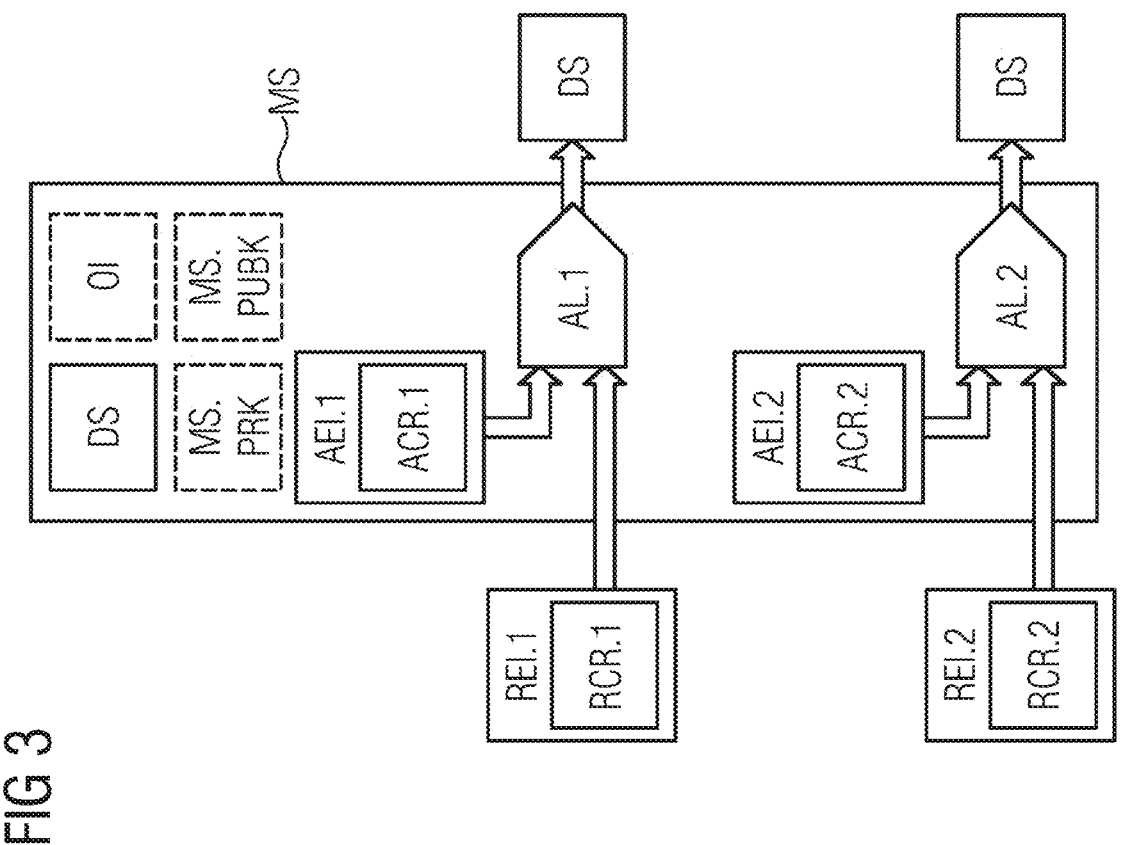
FIG. 3 shows a schematic view of a microservice.
Figure 2:
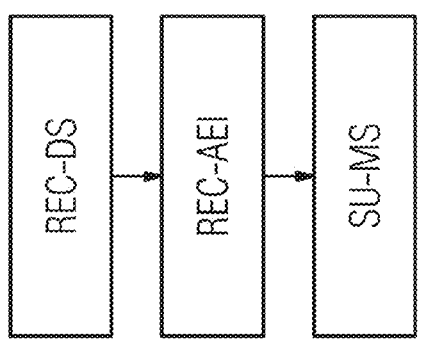
FIG. 2 shows a flow chart of a first embodiment of the method for setting up a microservice.

FIG. 2 displays a flow chart of a first embodiment of the method for setting up SU-MS a microservice MS. The resulting microservice MS is displayed in FIG. 3.

In this embodiment, the microservice MS comprises a medical dataset DS in an encrypted form, optional the microservice MS comprises owner information OI describing the owner of the medical dataset DS, a first access logic AL.1 based on a first accessing entity information AEI.1 and a second access logic AL.2 based on a second accessing entity information AEI.2.

In this embodiment the first accessing entity information AEI.1 comprises first access credentials ACR.1, and the second accessing entity AEI.2 information comprises second access credentials ACR.2. Optionally the accessing entity informations AEI.1, AEI.2 and/or the access logics AL.1, AL.2 can comprise further data, e.g. a name of the accessing entity AE, an expiration date which defines the end of the access granted, or counter which describes the maximal number of accesses. In general a microservice MS can comprise an arbitrary number of access logics AL.1, AL.2 based on accessing entity information, in particular only one access logic AL.1, AL.2.

Furthermore, in this embodiment the microservice MS comprises a private key MS.PRK and a public key MS.PUBK, wherein the plain medical dataset is stored asymmetrically encrypted with the public key MS.PUBK and wherein the plaintext medical dataset DS can be decrypted using the private key MS.PRK. The private key can be stored in a hidden way and/or randomly in the microservice MS, so that even an eavesdropper having access to the microservice MS cannot read out the private key and cannot decrypt the medical dataset DS.

Alternatively, the microservice MS can store the medical dataset DS chopped and/or randomly within an associated storage. In this case, the microservice MS does not need to comprise a public key MS.PUBK and a private key MS.PRK, and storing the medical datasets DS in an encrypted way is equivalent with storing the medical dataset DS in a hidden way. Alternatively, the microservice MS can also store the medical dataset DS symmetrically or asymmetrically encrypted with a key stored outside of the microservice, e.g. with a key associated with the owner information CI of the owner of the medical dataset DS (which is in general the patient PAT which is the basis for the medical dataset). Alternatively, the microservice MS can also store the medical dataset DS symmetrically or asymmetrically encrypted with a key based on the accessing entity information AEI.1, AEI.2 and/or based on the access credentials ACR.1, ACR.2.

The first step of the first embodiment of the method for setting up SU-MS a microservice MS displayed in FIG. 1 is receiving REC-DS a medical dataset DS. In this embodiment, the medical dataset DS comprises imaging data of a patient PAT, wherein the patient PAT is the owner of the medical dataset DS. Alternatively, the medical dataset DS may comprise other data, e.g. laboratory or diagnostic data related to the patient PAT. In this embodiment, the patient PAT decides to share this imaging data on the one hand side with his general practitioner, and on the other hand side with all emergency physicians of his home country.

The second step of the displayed first embodiment is receiving REC-AEI accessing entity information AEI.1, AEI.2 describing at least one accessing entity AE. The step of receiving REC-AEI accessing entity information AEI.1, AEI.2 can be executed multiple times, once for each accessing entity AE. In this embodiment there are two accessing entities AE, the first accessing entity AE is the set of emergency physicians and the second accessing entity AE is the single general practitioner of the patient, so the first accessing entity information AEI.1 describes the first accessing entity AE formed by the set of emergency physicians, and the second accessing entity information AEI.2 describes the second accessing entity AE formed by the general practitioner of the patient.

In the first embodiment, the first accessing entity information AEI.1 comprises first access credentials ACR.1, and the second accessing entity information AEI.1 comprises second access credentials ACR.2. Furthermore, in this first embodiment the first access credentials ACR.1 are an access certificate ACC-CERT related to an organization of emergency physicians of the country of the patient, whereas the second access credentials ACR.2 are an access token being a secret piece of digital information shared between the patient PAT and his general practitioner.

The third step of the displayed first embodiment is setting up the microservice MS based on the accessing entity information AEI.1, AEI.2, wherein the microservice MS contains the medical dataset DS in an encrypted form, wherein the microservice MS comprises an access logic AL.1, AL.2 based on the accessing entity information AEI.1, AEI.2 and wherein the access logic AL.1, AL.2 defines access conditions to the medical dataset DS and is configured to grant access to the medical dataset if the access conditions are fulfilled. The first access logic AL.1 is configured to grant access or to deny access to the medical dataset DS based on a first requesting entity information REI.1, and the second access logic AL.2 is configured to grant access or to deny access to the medical dataset DS based on a second requesting entity information REI.2.

In this embodiment, the access logic AL.1, AL.2 is a function taking as an input the accessing entity information AEI.1, AEI.2 and a requesting entity information REI.1, REI.2, in particular an access credential ACR.1, ACR.2 contained in the accessing entity information AEI.1, AEI.2 and a request credential RCR.1, RCR.2 contained in the requesting entity information REI.1, REI.2. The access logic AL.1, AL.2 gives as an output the medical dataset DS or information to access the medical dataset DS. The access logic AL.1, AL.2 might be part of an application programming interface (an acronym is "API").

In this embodiment, the access condition of the first access logic AL.1 is fulfilled if the request certificate RE-CT corresponding to the first request credential RCR.1 is related to the access certificate ACC-CERT corresponding to the first access credential ACR.1. In other words, the access condition of the first access logic AL.1 is fulfilled if the first requesting entity RE is an emergency physician certified by the first accessing entity AE, the organization corresponding to the set of all emergency physicians of a country.

The access condition of the second access logic AL.2 is fulfilled if the request token corresponding to the second request credential RCR.2 is equal to the access token corresponding to the second access credential ACR.2. In other words, the access condition of the second access logic AL.2 is fulfilled if the second requesting entity RE is the general practitioner of the patient being able to provide the shared secret token.

Figure 4:
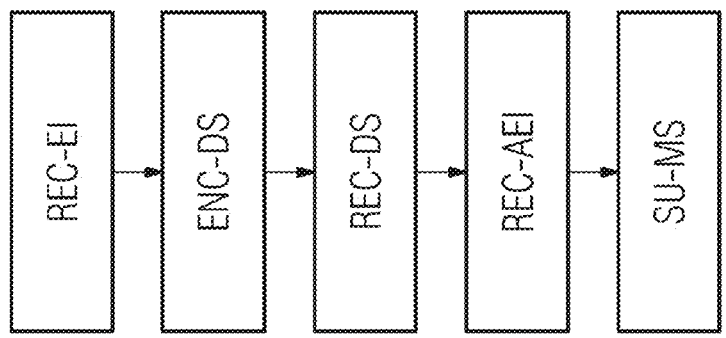
FIG. 4 shows a flow chart of a second embodiment of the method for setting up a microservice.

FIG. 4 displays a flow chart of a second embodiment of a method for setting up SU-MS a microservice MS. In this embodiment the method furthermore comprises the step of receiving REC-EI encryption information and the step of encrypting ENC-DS the medical dataset based on encryption information. The step of receiving REC-DS the medical dataset, the step of receiving REC-AEI accessing entity information AEI.1, AEI.2 and the step of setting up SU-MS the microservice MS based on the accessing entity information AEI.1, AEI.2 are equivalent to the respective steps of the first embodiment of the method for setting up SU-MS a microservice MS and may comprise all advantageous enhancements and alternatives described for the first embodiment in FIG. 2.

In this second embodiment the steps of receiving REC-EI the encryption information and the step of encrypting ENC-DS the medical dataset DS based on the encryption information are executed in an encryption separate from the providing unit executing the steps of receiving REC-DS the medical dataset, the step of receiving REC-AEI the accessing entity information AEI.1, AEI.2 and the step of setting up SU-MS the microservice. In particular, the the encryption unit may be in communication with the providing unit. In particular, the encryption unit may be identical with or part of the medical system creating the medical dataset DS. In other words, in this second embodiment, the providing unit receives the medical dataset DS already in an encrypted form. This implies that in this second embodiment the medical dataset DS cannot be decrypted by the microservice MS, so that the microservice MS or its access logic AL.1, AL.2 can only provide the medical dataset DS in an encrypted form.

Figure 5:
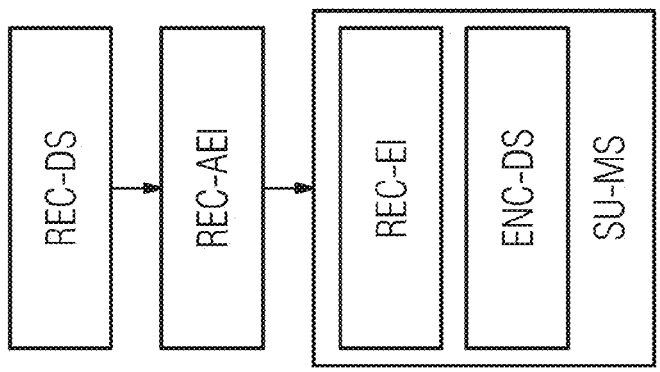
FIG. 5 shows a flow chart of a third embodiment of the method for setting up a microservice.

FIG. 5 displays a flow chart of a third embodiment of a method for setting up SU-MS a microservice MS. In this embodiment, the step of setting up SU-MS the microservice MS comprises the substep of receiving REC-EI encryption information, and the substep of encrypting ENC-DS the medical dataset DS using asymmetric or symmetric encryption based on the encryption information. The step of receiving REC-MS a medical dataset and the step of receiving REC-AEI accessing entity information AEI.1, AEI.2 are equivalent to the respective steps of the first embodiment of the method for setting up SU-MS a microservice MS and may comprise all advantageous enhancements and alternatives described for the first embodiment in FIG. 2.

In this third embodiment the microservice MS receives the medical dataset DS in a non-encrypted form (or in other words, the microservice MS receives the medical dataset DS in plaintext). The medical dataset DS is not stored in the non-encrypted form, but is encrypted ENC-DS by the providing unit setting up the microservice. In particular, the encryption information can be identical with, contained by or based on the accessing entity information AEI.1, AEI.2, in this case the step of receiving REC-EI the encryption information and the step of receiving REC-AEI the accessing entity information AEI.1, AEI.2 are identical, and the encryption information can be derived from the accessing entity information AEI.1, AEI.2.

Figure 6:
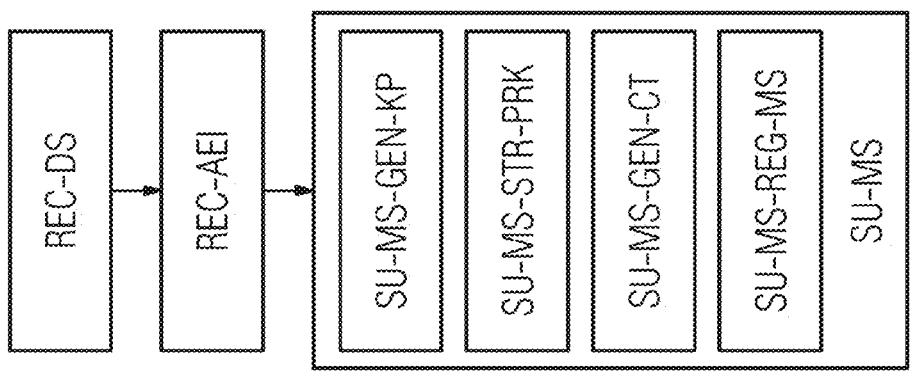
FIG. 6 shows a flow chart of a fourth embodiment of the method for setting up a microservice.

FIG. 6 displays a flow chart of a fourth embodiment of a method for setting up SU-MS a microservice MS. The step of receiving REC-MS a medical dataset DS and the step of receiving REC-AEI accessing entity information AEI.1, AEI.2 are equivalent to the respective steps of the first embodiment of the method for setting up SU-MS a microservice MS and may comprise all advantageous enhancements and alternatives described for the first embodiment in FIG. 2.

In this fourth embodiment, the step of setting up SU-MS a microservice comprises the substeps of generating SU-MS-GEN-KP a key pair comprising a public key MS.PUBK and a private key MS.PRK, the substep of storing SU-MS-STR-PRK the private key MS.PRK in a hidden way, the substep of generating SU-MS-GEN-CT a certificate and the substep of registering SU-MS-REG-MS the microservice MS.

Within the substep of generating SU-MS-GEN-KP a key pair, both a private key MS.PRK and a corresponding public key MS.PUBK are generated, wherein the public key MS.PUBK can be communicated to the outside of the microservice MS and the private key MS.PRK must not be communicated to the outside of the microservice MS. The public key MS.PUBK can be used for encrypting messages and data sent to the microservice MS. The private key MS.PRK can be used by the microservice MS to sign messages and data sent from the microservice MS, and to decrypt data sent to the microservice MS.

The key pair comprising the private key MS.PRK and the public key MS.PUBK may be generated for example based on integer factorization (using at least one of the "Benaloh" cryptosystem, the "Blum-Goldwasser" cryptosystem, the "Cayley-Purser" cryptosystem", the "Damgård-Jurik" cryptosystem, the "GMR" algorithm, the "Goldwasser-Micali" cryptosystem, the "Paillier" cryptosystem, the "Rabin" cryptosystem, the "RSA" cryptosystem, the "Okamoto-Uchiyama" cryptosystem, or the "Schmidt-Samoa" cryptosystem). Alternatively it can be generated based on the calculation of the discrete logarithm, in particular on elliptic curves (for example one of the algorithms or cryptosystems "Cramer-Shoup", "Diffie-Hellmann", "DSA", "ECDH", "ECDSA", "EdDSA", "EKE", "ElGamal", "MQV", "Schnorr", "SPEKE", "SRP" or "STS"). Alternatively, it can be generated based on other asymmetrical algorithms or cryptosystems (e.g. "AE", "CEILIDH", "EPOC", "HFE", "IES", "Lamport", "McEliece", "Merkle-Hellman", "Naccache-Stern", "Naccache-Stern knapsack", "NTRUEncrypt", "NTRUSign", Three-pass protocol", "XTR"). It can also be based on the Diffie-Hellman key exchange protocol, based on the digital signature algorithm, based on elliptic curve cryptography, based on password-authenticated key agreement cryptography, based on the "Paillier" cryptosystem, based on the RSA encryption algorithm, or based on the YAK authenticated key agreement protocol.

Within the substep of storing SU-MS-STR-PRK the private key MS.PRK in a hidden way, the private key MS.PRK is stored such that it is not accessible from the outside. For example, the private key MS.PRK can be stored in a memory location which can only be accessed by the microservice MS, and not by another process or program running on the server hosting the microservice MS. In particular, the private key MS.PRK can be stored using the techniques of Secure Memory Encryption (acronym "SME") and Secure Encrypted Virtualization (acronym "SEV"). Alternatively or additionally, the private key MS.PRK can be stored in a fragmented way. Alternatively or additionally, the memory location to store the private key MS.PRK may be secured by hardware measures.

The substep of generating SU-MS-GEN-CT a certificate may be executed by the microservice MS itself, by a certificate authority CA, by the owner of the microservice and/or by the accessing entity AE. The substep of generating SU-MS-GEN-CT may comprise the generation of a signature of data or information belonging to the microservice MS, in particular of an identifier of the microservice, an URL of the microservice and/or a hash value of the plaintext of the medical dataset DS contained in the microservice. In particular, the data or information belonging to the microservice MS can also comprise the public key MS.PUBK of the microservice MS. The certificate may then be communicated to the outside.

In this fourth embodiment, the fourth substep of the step of setting up SU-MS the microservice MS is registering SU-MS-REG-MS the microservice. In particular, the URL to access the microservice MS can be communicated to the entity creating the microservice MS, or to other entities using the microservice MS. Furthermore, a ledger of microservices LDG-MS can be enhanced with the newly created microservice MS.

TABLE A

Definition of a microservice

| | |
|---|---|
| A.1 | class microservice: |
| A.2 | private data |
| A.3 | private owner |
| A.4 | private acc_creds[ ] |
| A.5 | private prev_ms_hash |
| A.6 | private ms_certificate |
| A.7 | private private_key |
| A.8 | private creation_time |
| A.9 | public set_up(new_data, new_owner, accessing_entities[ ], prev_ms = Nothing) |
| A.10 | public get_data(req_cred) |
| A.11 | public get_data(req_cred, pub_key) |
| A.12 | public get_certificate: return self.certificate |
| A.13 | public hash ( ) : return SHA256(self.data & self.owner & self.creation_time) |

Table A shows pseudocode defining a prototype for a microservice MS as a class in an object oriented programming environment. A microservice MS itself would be an instance of this prototype class. In line A.2 the microservice MS comprises the private variable "data", which cannot be accessed directly from outside. The variable "data" corresponds to the medical dataset DS stored in an encrypted form. In line A.3 the microservice comprises the private variable "owner", which corresponds to the owner information CI describing the owner of the medical dataset DS. The variable "owner" is an optional variable and can be empty. In line A.4 the microservice comprises the variable "acc_cred[ ]", which is an array of access credentials ACR-1, ACR-2. This array of access credentials ACR-1, ACR-2 can comprise an arbitrary number of access credentials ACR-1, ACR-2, in particular the array may comprise only one access credential ACR-1, ACR-2. In line A.5 the microservice MS comprises the private variable "prev_" which stores a hash value of the previous microservice stored in a ledger containing microservices. The private variable "prev_ms_hash" is an optional variable and can be empty. In line A.6 the microservice MS comprises a certificate stored in the variable "ms_certificate". The variable "ms_certificate" comprises an identifier "ID" of the microservice MS, a public key "public_key" of the microservice MS and a signature "sign" of the microservice. The variable "ms_certificate" is an optional variable and can be empty. The certificate can be accessed using the function "get_( )" in line A.11. Furthermore, in line A.7 the microservice comprises the variable "private_key", which is the private_key corresponding to the public_key stored in the variable "ms_certificate". The variable "private_key" cannot be accessed from outside of the class. In line A.8 the microservice comprises a variable "creation_time" storing the creation time of the microservice. The variable "creation_time" is an optional variable and can be empty.

The pseudocode comprises a function "set_up" which is used for setting up the microservice. In particular, the displayed class is a prototype of a microservice MS, and each microservice is an instance of this prototype class, which can be initiated with the "set_up" function. In particular, the function "set_up" can be interpreted as a constructor function of the microservice prototype class. Furthermore the microservice comprises a function "get_data" for checking credentials and granting access to the internal data. Pseudocode for the function "set_up" is given in table B, pseudocode for the functions set "get_data" is given in tables C and D. Furthermore the microservice comprises a function "hash( )" which returns a hash value of the internal data of the microservice.

In this embodiment the "SHA256" hash function is used. Other known cryptologic hash functions are e.g. "Snefru", "N-Hash", "FFT-Hash", "MD4", "MD5", "SHA" (in particular "SHA-0", "SHA-1", "SHA-256", "SHA-384" and "SHA-512"), "RIPEMD", "HAVAL", "TIGER", "PANAMA", "WHIRLPOOL", "SMA SH", "FORK-256", "SHA-3", "BLAKE", or other hash functions based on the Merkle-Damgård construction or on the Sponge construction.

TABLE B

Setting up a microservice

| | |
|---|---|
| B.1 | public microservice::set_up(new_data, new_owner, accessing_entities[ ], prev_ms = Nothing): |
| B.2 | self.creation_time = time( ) |
| B.3 | self.owner = new_owner |
| B.4 | self.prev_ms_hash = prev_ms.hash( ) |
| B.5 | self.certificate = ca.certify(self.hash( ), public_key) |
| B.6 | self.acc_creds = [ae.get_certificate( ) for ae in accessing_entities] |
| B.7 | public_key, self.private_key = generate_key_pair( ) |
| B.8 | self.data = encrypt(new_data, public_key) |

Table B shows pseudocode for setting up a microservice. In this embodiment the variable "new_data" corresponds to a medical dataset, and the internal variable "self.data" corresponds to the encrypted form of the medical dataset.

In the code lines B.2 to B.6 the internal variables "creation_time", "owner", "prev_ms_hash", "certificate" and "acc_" are assigned based on the given parameters. For the "creation_", the current time is determined using a system function "time( )". The variable "prev_ms_hash", which stores a hash of the previous microservice MS in the ledger, is calculated using the "hash( )" function of the given previous microservice "prev_ms" Optionally one could include a functionality to handle the situation where the microservice MS being set up is the first microservice without any previous microservice (this would be a test whether the variable "prev_ms" is "Nothing", and in this case assign also the value "Nothing" to the variable "prev_ms_hash").

In line B.5 a certificate of the microserivce MS is created by calling the function "certify" of a certificate authority CA. The certificate authority CA in general signs the certificate with a private key belonging to the certificate authority CA. It is also possible that the certificate authority CA is identical to one or more of the accessing entities AE.

If the access credential is an access certificate ACC-CERT, the certificate created in B.5 can also be derived from the access certificate ACC-CERT if the private key related to the access certificate ACC-CERT additionally signs the certificate. Therefor the accessing entity AE has to sign the certificate with the private key, because in general the private key related to the access certificate ACC-CERT is not available to the certificate authority. If the access credential is an access token and not an access certificate ACC-CERT, the certificate created in B.5 can also be derived from the access token by storing a hash of the access token in the certificate.

In line B.6, the internal variable "self.acc_creds" is filled with the one or more access credentials ACR.1, ACR.2. The displayed pseudocode corresponds to the case where the access credentials ACR.1, ACR.2 are on or more access certificates ACC-CERT belonging to one or more accessing entities AE, in other word the microservice stores copies of the access certificates ACC-CERT belonging to one or more accessing entities AE. The displayed structure on the right hand side of the code line B.6 creates an array comprising the certificates of the accessing entities AE, using the function "get_( )" on each of the accessing entities AE.

If in an alternative case the access certificates ACC-CERT belong to the microservice, and the access certificates ACC-CERT are directly authorized by one or more certificates AE.CT belonging to the accessing entity AE, the code line B.6 can be changed to "self.acc_creds=[ae.derive_certificate ( ) for ae in accessing_entities]", where the function "derive_certificate" derives an access certificate ACC-CERT from the certificate AE.CT belonging to the accessing entity AE. This function can take as an argument a parameter identifying the microservice, e.g. a parameter comprising (a hash of) the timestamp, a hash of the medical dataset DS, and (a hash of) the owner information OI, or alternatively the certificate of the microservice MS. Optionally in this case the private keys belonging to the access certificates can be stored within the microservice.

Figure 14:
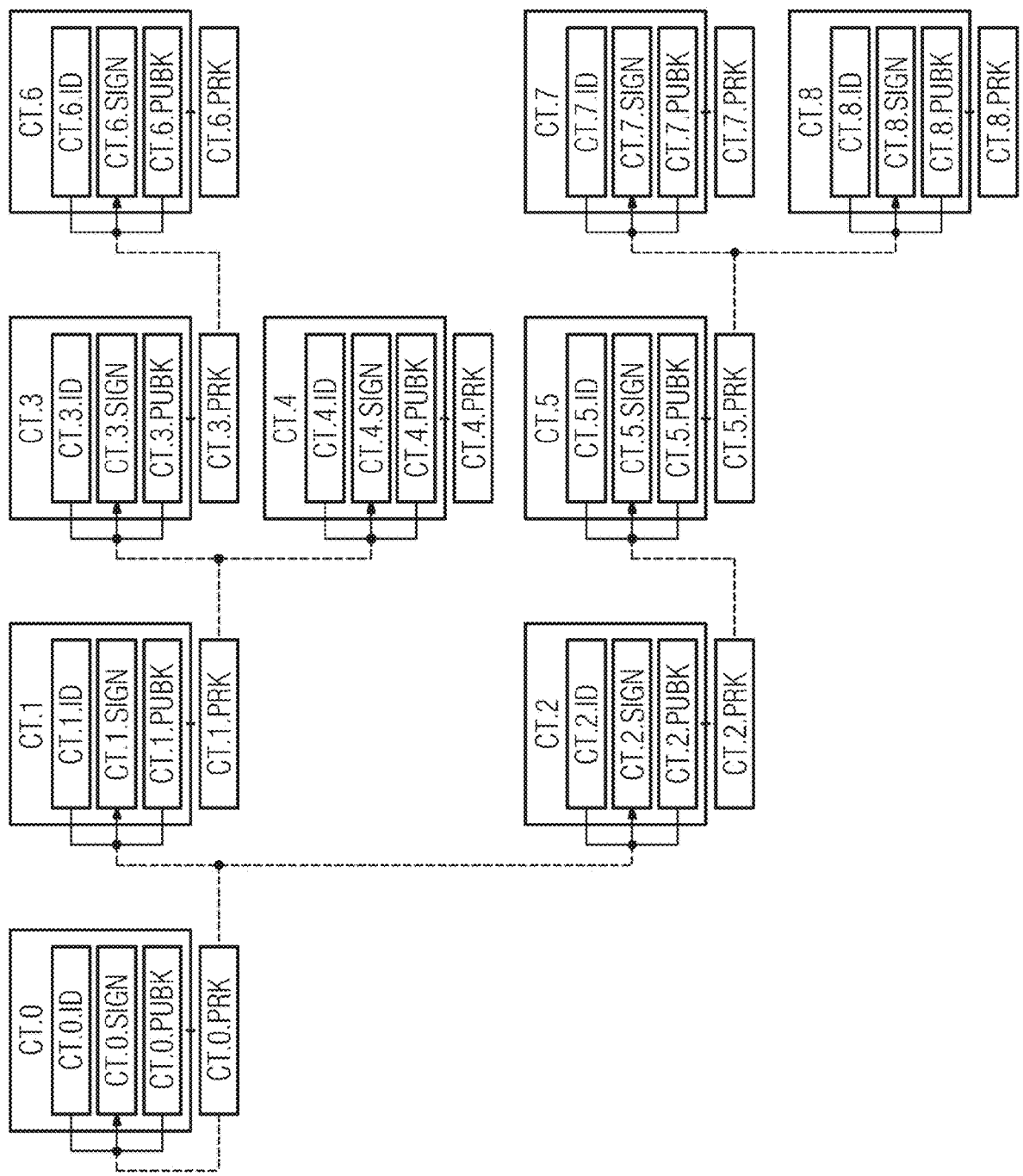
FIG. 14 shows a first embodiment of a certificate tree.

The function "derive_certificate( )" can induce the accessing entity AE to create and/or sign the access certificate, leading to a certificate structure displayed in FIG. 14. Alternatively, a certificate authority CA can create and/or sign the access certificate, leading to a certificate structure displayed in FIG. 15, and the authorization of the accessing entity can be stored in an access ledger LDG-CT as displayed in FIG. 16.

If in an alternative case the credentials ACR.1, ACR.2 are one or more tokens or shared secrets shared with one or more accessing entities AE. In this case, the line B.6 can be changed to "self.acc_creds=[ae.get_token( ) for ae in accessing_entities]", wherein the function "get_token( )" creates a shared secret and stores the shared secret also related to the accessing entity AE.

In the code line B.7 an asymmetric pair of keys comprising a public key and a private key is generated. Therefor any asymmetric key generation algorithm can be used, which is represented here by the generic function "generate_key_pair( )". The newly generated public key "public_key" is then used in code line B.7 to asymmetrically encrypt the medical dataset given as a parameter and to store the encrypted medical dataset in the internal variable data. The private key has to be stored in a way that it cannot be read from outside, e.g. in a certain memory hardware or in a randomized way.

Figure 8:
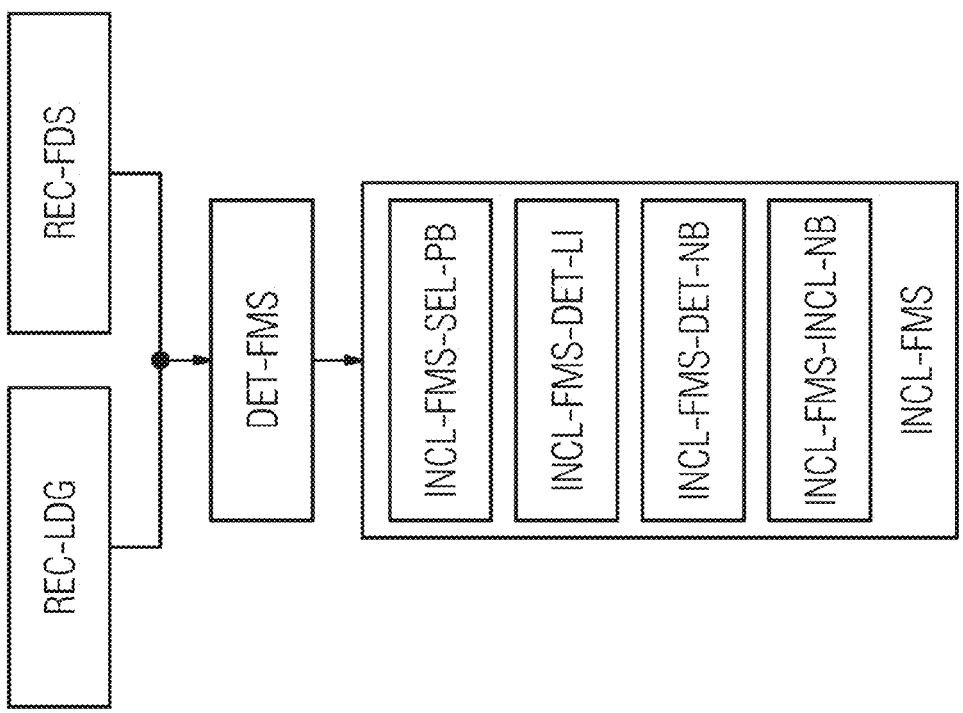
FIG. 8 shows a flow chart of a second embodiment of the method for enhancing a ledger with a further microservice.
Figure 7:
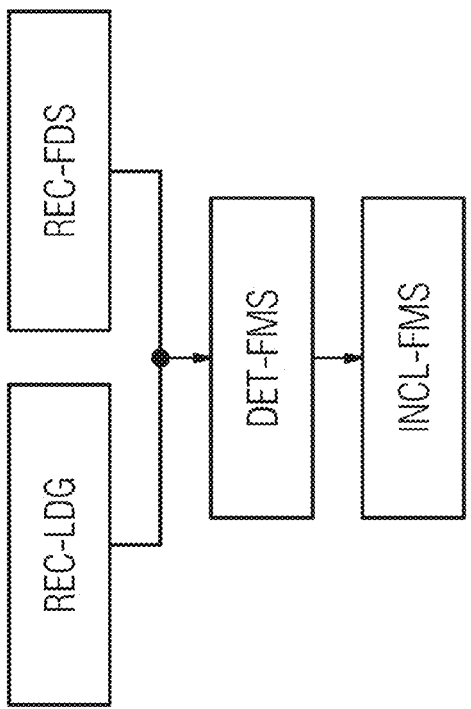
FIG. 7 shows a flow chart of a first embodiment of the method for enhancing a ledger with a further microservice.

FIG. 7 displays a flow chart of a first embodiment of a method for enhancing a ledger LDG-MS with a further microservice FMS, FIG. 8 displays a flow chart of a second embodiment of a method for enhancing a ledger LDG-MS with a further microservice FMS.

The first step of the first embodiment of the method for enhancing a ledger LDG-MS with the further microservice FMS is receiving REC-LDG the ledger LDG-MS, wherein the ledger LDG-MS contains microservices MS, wherein each of the microservices MS contains a medical dataset DS in an encrypted form and comprises an access logic AL.1, AL.2 to the medical dataset DS.

Figure 9:
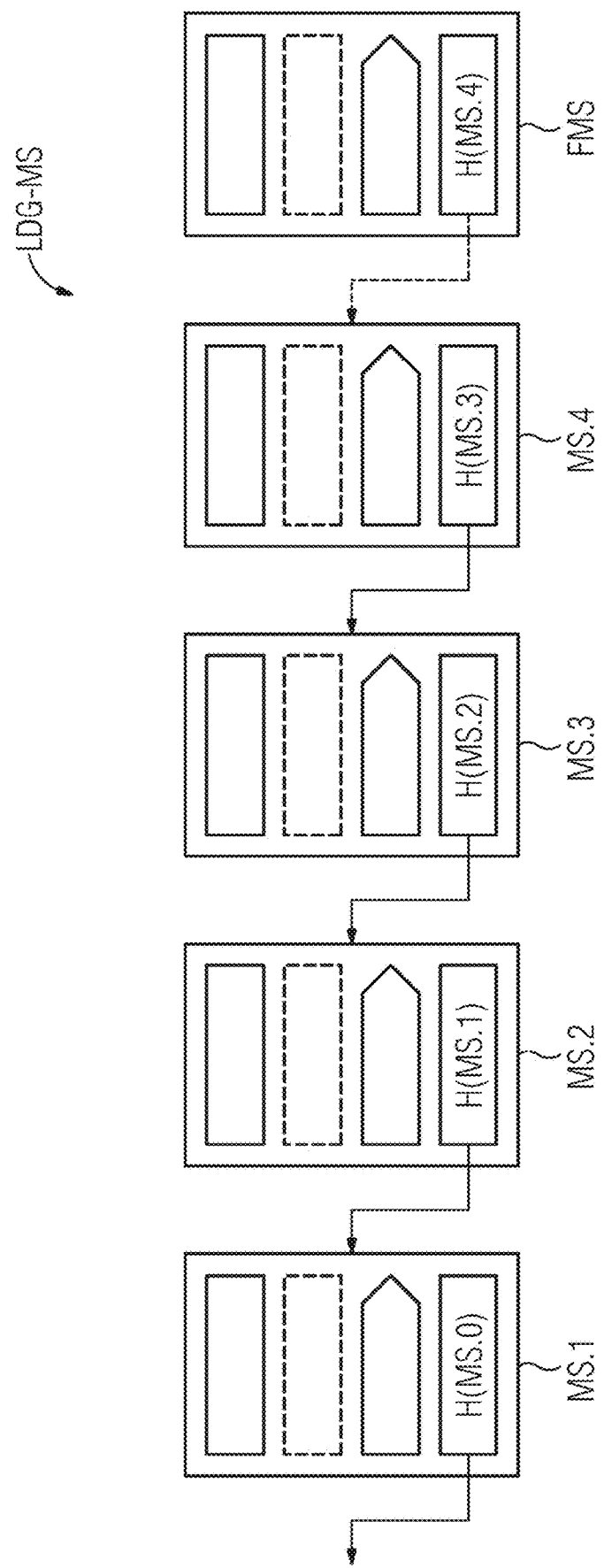
FIG. 9 shows an embodiment of a ledger comprising microservices.

FIG. 9 shows a first embodiment of a ledger LDG-MS containing microservices, FIG. 10 shows a second embodiment of a ledger LDG-MS containing microservices.

In the first embodiment displayed in FIG. 9 a ledger LDG-MS comprises the microservices MS.1, . . . , MS.4 itself. In this embodiment, the ledger LDG-MS comprises the compiled machine code corresponding to the microservices MS.1, MS.4. Alternatively, the ledger LDG-MS can comprise the source code of the microservices MS.1, . . . , MS.4 and the data associated with the microservice, the data comprising the medical dataset DS. Alternatively, the ledger LDG-MS may comprise other data fully defining the respective microservice MS.1, . . . MS.4. In this embodiment each microservice MS.1, . . . , MS.4 comprises a single hash H(MS.0), . . . , H(MS.3) of the preceding microservice. This hash H(MS.0), . . . , H(MS.3) links the microservices MS.1, . . . , MS.4 and creates a blockchain structure. By using the hash H(MS.0), . . . , H(MS.3) of the preceding microservice, a change of any microservice in the blockchain can be detected.

In the displayed first embodiment of a ledger LDG-MS, each microservice MS.1, . . . , MS-4 of the ledger LDG-MS (except the first microservice) has exactly one preceding microservice, and each microservice MS.1, . . . , MS.4 of the ledger LDG-MS (except the last microservice) is the parent for exactly one other block. Another word for the displayed and described ledger LDG-MS is "blockchain". Alternatively, the ledger LDG-MS can also comprise sidechains. Alternatively, the structure of the ledger LDG-MS can be a tree instead of a chain, another word for such a ledger is "blocktree". Alternatively, the structure of the ledger LDG-MS can be a directed acyclic graph, another word for such a ledger is "tangle".

In this first embodiment the ledger LDG-MS comprises only microservices MS.1, . . . , MS.4. It is also possible that the ledger LDG-MS comprises other data blocks, which can be unrelated to the microservices or to healthcare data in general. In this case the microservices MS.1, . . . , MS.4 contained in the ledger LDG-MS do not comprises hashes of preceding microservices, but hashes of preceding datasets in the ledger LDG-MS.

In the second embodiment displayed in FIG. 10 a ledger LDG-MS comprises blocks MSB.1, . . . , MSB.4, wherein each block MSB.1, . . . , MSB.4 corresponds to a microservice MS. The ledger LDG-MS can comprise further blocks not corresponding to a microservice MS. In this embodiment, each of the blocks MSB.1, . . . , MSB.4 comprises an address ADDR.1, . . . , ADDR.4 of the microservice MS it corresponds to, a hash value H(DS.1), H(DS.4) of the medical dataset DS contained in the microservice MS it corresponds to, and a hash value H(MSB.0), . . . , H(MSB.3) of the parent block MSB.1, . . . , MSB.4 in the ledgers LDG-MS. By storing the hash value H(DS.1), . . . , H(DS.4) of the medical dataset DS contained in the microservice MS it corresponds to manipulation to the dataset DS or man-in-the-middle attacks can be detected by comparing the stored hash values hash value H(DS.1), . . . , H(DS.4) to the hash value of the dataset DS received from the microservice MS.

In the displayed second embodiment of a ledger, each block MSB.1, . . . , MSB.4 of the ledger LDG-MS (except the first block) has exactly one parent block, and each block MSB.1, . . . , MSB.4 of the ledger LDG-MS (except the last block) is the parent for exactly one other block. Another word for the displayed and described ledger LDG-MS is "blockchain". Alternatively, the ledger LDG-MS can also comprise sidechains. Alternatively, the structure of the ledger LDG-MS can be a tree instead of a chain, another word for such a ledger is "blocktree". Alternatively, the structure of the ledger LDG-MS can be a directed acyclic graph, another word for such a ledger is "tangle".

The second step of the first embodiment of the method for enhancing the ledger LDG-MS with the further microservice FMS is receiving REC-FDS a further medical dataset FDS. The step of receiving REC-FDS a further medical dataset FDS can be executed before the step of receiving REC-LDG the ledger LDG-MS, after the step of receiving REC-LDG the ledger LDG-MS or in parallel with the step of receiving REC-LDG the ledger LDG-MS. The further medical dataset FMS can comprise all advantageous enhancements and alternatives described for the medical dataset DS above.

The third step of the embodiment of the method for enhancing the ledger LDG-MS with the further microservice FMS is providing PROV-FMS the further microservice FMS containing the further medical dataset FDS in an encrypted form and comprising an access logic to the further medical dataset FDS. The further microservice FMS can be set up for example with one of the methods described in FIG. 2 and FIG. 4 to FIG. 6, wherein the further medical dataset FMS corresponds to the dataset DS and the further microservice FMS corresponds to the MS described in FIG. 2 and FIG. 4 to FIG. 6.

The fourth step of the embodiment of the method for enhancing the ledger with the further microservice FMS is including INCL-FMS the further microservice FMS into the ledger LDG-MS. For including the further microservice FMS into the first embodiment of the ledger LDG-MS displayed in FIG. 9, the compiled machine code corresponding to the further microservice FMS has to be included into the ledger LDG-MS by appending the further microservice to the ledger LDG-MS. For including the further microservice FMS into the second embodiment of the ledger LDG-MS displayed in FIG. 10, the respective data of the further microservice FMS, in particular an address ADDR-FMS of the further microservice and a hash H(FDS) of the further medical dataset contained in a further microservice block FMSB has to be included into the ledger LDG-MS by appending the further microservice block FMSB to the ledger LDG-MS.

FIG. 8 displays a flow chart of a second embodiment of the method for enhancing a ledger LDG-MS with a further microservice FMS. The steps of receiving REC-LDG the ledger LDG-MS, of receiving REC-FDS a further medical dataset FDS and of providing PROV-FMS the further microservice FMS are identical with the respective steps displayed in and described for FIG. 7 and/or the first embodiment and may comprise all their possible advantageous enhancements or alternative embodiments.

The second embodiment is described for the second embodiment of the ledger LDG-MS, but can be applied also for the first embodiment of the ledger with minor changes obvious for a person skilled in the art.

In this second embodiment, the step of including INCL-FMS the further microservice FMS into the ledger LDG comprises the substep of selecting INCL-FMS-SEL-PB a parent data block MSB.4 of the ledger LDG-MS, the substep of determining a link information INCL-FMS-DET-LI based on the parent data block MSB.4, the substep of determining INCL-FMS-DET-NB a further data block FMSB for the ledger LDG-MS, and the substep of including INCL-FMS-INCL-NB the further data block FMSB into the ledger LDG-MS.

In this second embodiment, the substep of selecting INCL-FMS-SEL-PB a parent data block MSB.4 of the ledger LDG-MS selects the last data block MSB.4 already present in the blockchain ledger LDG-MS of microservices. If the ledger LDG-MS is not a linear blockchain, but e.g. a blocktree or a tangle, within the substep of selecting INCL-FMS-SEL-PB a parent data block MSB.4 of the ledger LDG-MS it is possible to choose between several data blocks MSB.1, . . . , MSB.4 already contained in the ledger LDG-MS. This choice can be based e.g. on a weight or a cumulative weight of data blocks MSB.1, . . . , MSB.4 already contained in the ledger LDG-MS. Alternatively the choice can be based on the patient PAT or the creator of the dataset DS of the microservice MS, so for example all microservices MS containing data of a certain patient PAT or all microservices MS with medical datasets DS created by a certain creator can be stored subsequently in the ledger LDG-MS.

In this second embodiment, the substep of determining a link information INCL-FMS-DET-LI based on the parent data block MSB.4 comprises the execution of a consensus mechanism. A consensus mechanism has to be included to ensure that every node in a network storing copies of the ledger LDG-MS stores the same or nearly the same version of the ledger LDB-MS (this is denoted as "synchronization problem"). Examples for a consensus mechanism are "proof of work", "proof of stake" and "proof of elapsed time". In this second embodiment a processor-restricted proof of work is used, which means that for example each block MSB.1, . . . , MSB.4, FMSB comprises an freely selectable integer number, that has to fulfill a certain condition. The condition here is that the hash of the block MSB.1, . . . , MSB.4, FMSB comprising the number must be smaller than a predefined value, and blocks MSB.1, . . . , MSB.4, FMSB are only considered as valid blocks if the predefined condition is fulfilled. Since calculating a hash function is a one-way function, several integer numbers have to be selected and the hash has to be calculated testwise until a correct value for the hash can be found.

In this embodiment, the link information is the hash H(MSB.1), . . . , H(MSB.4) of the previous block in the ledger LDG-MS, wherein the hash function is based on the previous block and the freely selectable integer number of the further block FMSB to be inserted.

FIG. 11 displays a flow chart of an embodiment of a method for accessing a medical dataset contained by a microservice MS in an encrypted form, wherein the microservice MS comprises an access logic AL.1, AL.2 based on an accessing entity information AEI.1, AEI.2, and wherein the access logic AL.1, AL.2 defines access conditions to the medical dataset DS. The microservice MS being accessed in this embodiment is displayed in FIG. 3, the microservice MS being accessed in this embodiment was set-up using the method displayed and described in FIG. 2.

The first step of the displayed method for accessing a medical dataset DS contained in a microservice MS is receiving REC-AR an access request to the medical dataset DS by a requesting entity RE.

In the displayed embodiment, the requesting entity RE calls the microservice MS by sending a request to the microservice MS, in particular an HTTP request to an URL corresponding to the microservice MS, which is then received by the microservice MS. In particular, the microservice MS can expose an API, in particular a REST-API to provide a function to be called by the requesting entity RE. In this embodiment the access request comprises request credentials RCR.1, RCR.2 of the requesting entity RE, which are in this embodiment a request certificate RE-CT of the requesting entity RE. Alternatively, the request credentials RCR.1, RCR.2 may also be a token which represents a shared secret shared between the microservice MS and the requesting entity RE.

The second step of the displayed method for accessing a medical dataset DS contained in a microservice MS is performing CHK-AR a check if the access conditions are met by the requesting entity RE.

In this embodiment, the check is based on the access credentials ACR-1, ACR-2 stored within the microservice MS and on request credentials RCR.1, RCR.2 submitted within the request to the microservice MS, wherein both the access credentials ACR-1, ACR-2 and the request credentials RCR.1, RCR.2 are digital certificates ACC-CERT, RE-CT. The digital certificates may form a certificate tree as displayed in FIG. 14 or FIG. 15.

Figure 12:
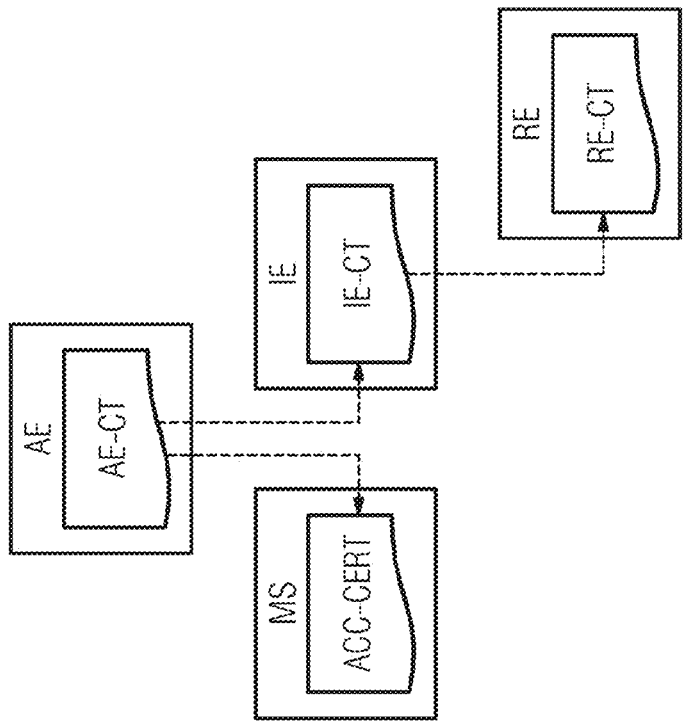
FIG. 12 shows a first embodiment of the certificate structure used to check an access request to a medical dataset contained by a microservice in an encrypted form.

In this embodiment the access certificate ACC-CERT belongs to the microservice MS and is directly authorized by a certificate AE-CT belonging to the accessing entity AE and the access certificate ACC-CERT is related to the request certificate RE-CT if the request certificate RE-CT is derived from the certificate AE-CT belonging to the accessing entity AE, which is displayed in FIG. 12. In other words, the microservice MS has access to the private key of the access certificate ACC-CERT, and the accessing entity AE does not have access to the private key of the access certificate ACC-CERT, but has access to the private key of the certificate AE-CT belonging to the accessing entity AE. In this embodiment, directly authorized means that there is no further certificate in authorization chain between the certificate AE-CT belonging to the accessing entity AE and the access certificate ACC-CERT. It is possible that the request certificate RE-CT is indirectly derived using intermediate certificates IE-CT, for example as displayed in FIG. 12, wherein the request certificate RE-CT is directly authorized by an intermediate certificate IE-CT belonging to an intermediate entity IE, and wherein the intermediate certificate IE-CT is directly authorized by the certificate AE-CT belonging to the accessing entity AE. Alternatively, the number of intermediate certificates IE-CT may be limited by the access logic AL-1 to a maximal number; in particular the maximal number can be one, which means that the request certificate RE-CT must be directly authorized by the certificate AE-CT belonging to the accessing entity AE.

Figure 13:
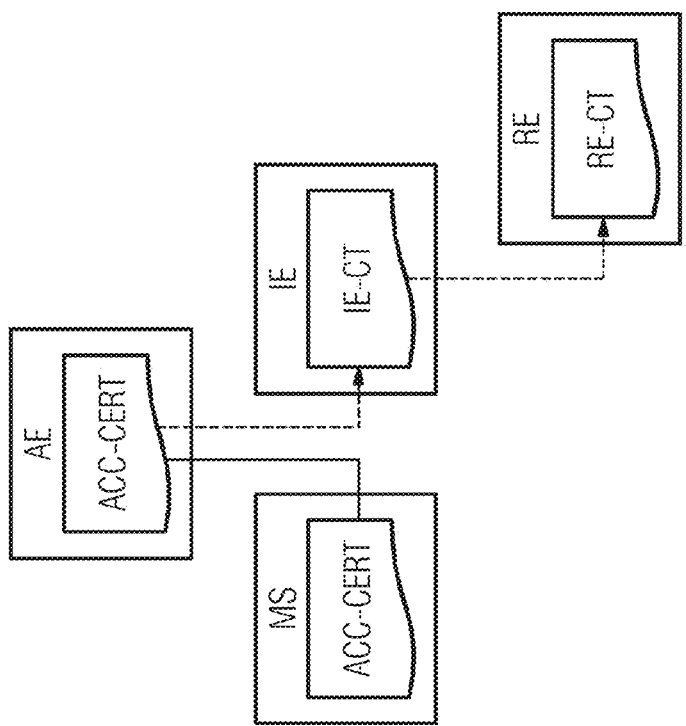
FIG. 13 shows a second embodiment of the certificate structure used to check an access request to a medical dataset contained by a microservice in an encrypted form.

In an alternative embodiment, the access certificate ACC-CERT belongs to the accessing entity AE and the access certificate ACC-CERT is related to the request certificate RE-CT if the request certificate RE-CT is derived from the access certificate ACC-CERT, which is displayed in FIG. 13. In other words, the microservice MS stores a copy of the access certificate ACC-CERT issued for the accessing entity AE, this means that the accessing entity AE has access to the private key corresponding to the access certificate ACC-CERT, and that the microservice MS does not have access to the private key corresponding to the access certificate ACC-CERT. It is possible that the request certificate RE-CT is indirectly derived using intermediate certificates IE-CT, for example as displayed in FIG. 13, wherein the request certificate RE-CT is directly authorized by an intermediate certificate IE-CT belonging to an intermediate entity IE, and wherein the intermediate certificate IE-CT is directly authorized by the access certificate ACC-CERT. Alternatively, the number of intermediate certificates IE-CT may be limited by the access logic AL-1 to a maximal number, in particular the maximal number can be one, which means that the request certificate RE-CT must be directly authorized by the access certificate ACC-CERT.

In both FIG. 12 and FIG. 13 the fact that a first certificate directly authorizes a second certificate is indicated by a dashed arrow from the first certificate to the second certificate. Certificates which are identical are connected by a solid line.

Alternatively, both the access credentials ACR-1, ACR-2 and the request credentials RCR.1, RCR.2 may be a token or a shared secret. In this case, access to the data will be granted if the token of the request credentials RCR.1, RCR.2 matches the token of the access credentials ACR-1, ACR-2, and access will be denied of the token of the request credentials RCR.1, RCR.2 does not match the token of the access credentials ACR-1, ACR-2.

It is also possible that the check is based on both a token as a shared secret and a digital certificate. The check can also be based on further conditions, for example a maximal number of accesses to a microservice MS, which can be tracked by using an access counter within the microservice MS. The maximal number of accesses can be counted for all accesses, or for accesses from a requesting entity RE. The access conditions can also be based on an expiration date, i.e. that access is only granted before or after a given date. Furthermore, the access conditions can also be based on the existence of further microservices MS, e.g. all access requests can be denied if there exists a further microservice MS with an updated medical dataset or with one or more updated access conditions.

The third step of the displayed method for accessing a medical dataset DS contained in a microservice MS is granting access GRNT-AR to the medical dataset DS to the requesting entity RE or denying access DNY-AR to the medical dataset DS depending on the result of the check.

If the access is granted, the medical dataset DS contained in the microservice MS in an encrypted form is decrypted and sent to the requesting entity RE. In particular, if the medical dataset DS was stored asymmetrically encrypted by a public key belonging to the microservice MS, the asymmetrical decryption of the medical dataset DS is based on the private key associated with the public key belonging to the microserivce MS. Advantageously, the medical dataset DS can be encrypted for sending to the requesting entity RE, in particular by using an asymmetrical encryption based on a public key belonging to the requesting entity RE. In particular, the public key belonging to the requesting entity RE can be send to the microservice MS within the access request, or the public key belonging to the requesting entity RE may be sent to the microservice MS in a second step.

FIG. 14 displays a first embodiment of a certificate tree comprising nine certificates CT.0, . . . , CT.8. In this embodiment, each certificate CT.0, . . . , CT.8 comprises an certificate identifier CT.0.ID, . . . , CT.8.ID, a public_key CT.0.PUBK, . . . , CT.8.PUBK and a signature CT.0.SIGN, . . . , CT.8.SIGN. For each of the public keys CT.0.PUBK, . . . , CT.8.PUBK there is an associated private key CT.0.PRK, . . . , CT.8.PRK that is not contained within the certificate CT.0, . . . , CT.8. The private keys CT.0.PRK, . . . , CT.8.PRK might be stored within the certified entities so that they cannot be accessed from outside the certified entity.

In this embodiment, the structure of the certificate tree is encoded in the signatures CT.0.SIGN, . . . , CT.8.SIGN of the certificate. Each of the signature CT.0.SIGN, . . . , CT.8.SIGN is a signature of the certificate identifier CT.0.ID, . . . , CT.8.ID and the public key CT.0.PUBK, . . . , CT.8.PUBK of the certificate signed with the private key CT.0.PRK, . . . , CT.8.PRK corresponding to the parent certificate CT.0, . . . , CT.8. For example, the signature CT.1.SIGN of the child certificate CT.1 is signed with the private key CT.0.PRK of the parent certificate CT.0, the data which is signed comprises the certificate identifier CT.1.ID and the public key CT.1.PUBK of the certificate CT.1.

In this embodiment, it can be checked whether a first certificate CT.0, . . . , CT.8 directly authorizes a second certificate CT.0, . . . , CT.8 by verifying that the signature CT.0.SIGN, . . . , CT.8.SIGN contained in the second certificate CT.0, . . . , CT.8 is actually created by the private key CT.0.PRK, . . . , CT.8.PRK of the first certificate CT.0, . . . , CT.8.

Figure 15:
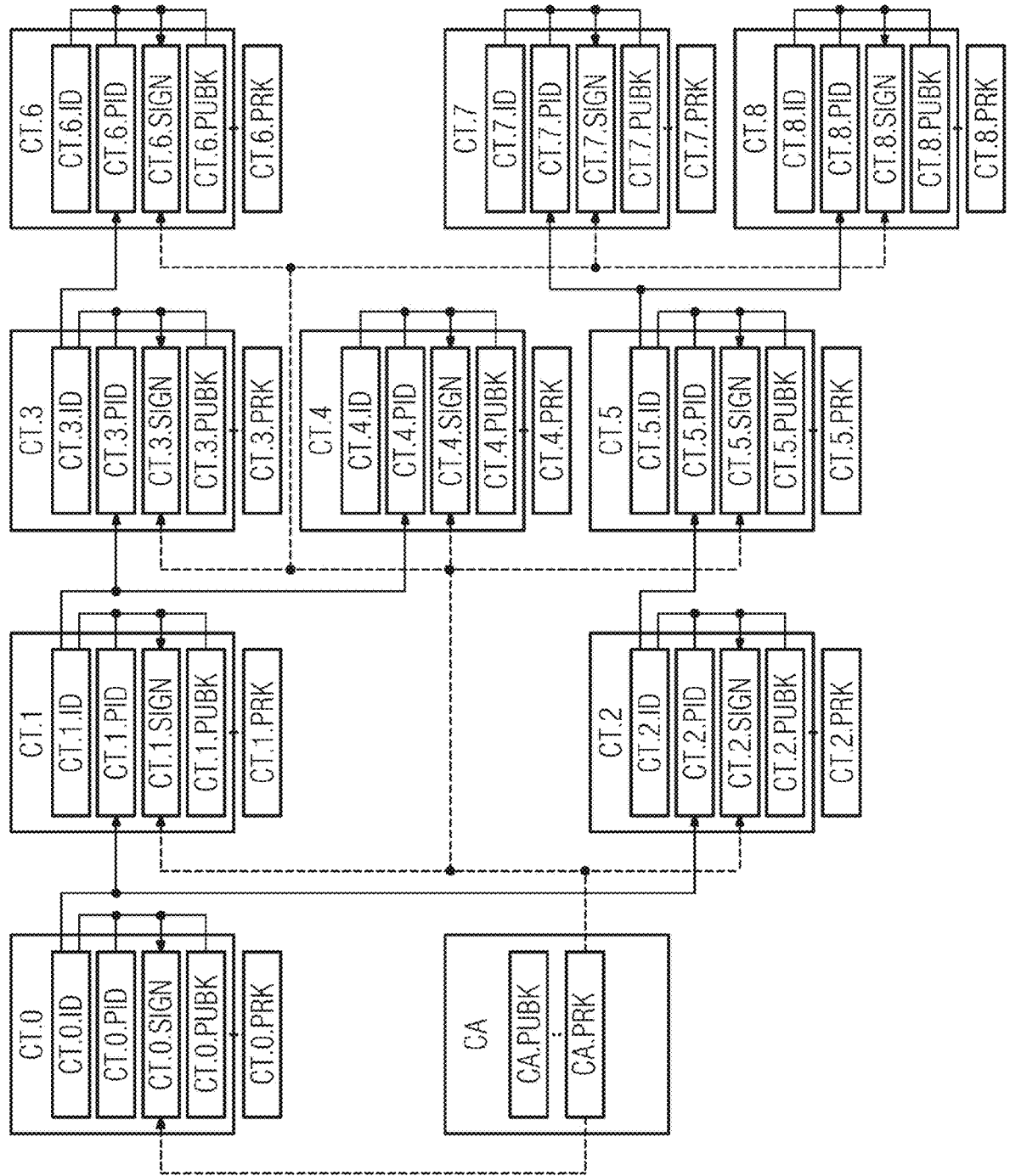
FIG. 15 shows a second embodiment of a certificate tree.

FIG. 15 displays a second embodiment of a certificate tree comprising nine certificate CT.0, . . . , CT.8. In this embodiment, each certificate CT.0, . . . , CT.8 comprises an certificate identifier CT.0.ID, . . . , CT.8.ID, a public key CT.0.PUBK, . . . , CT.8.PUBK and a signature CT.0.SIGN, . . . , CT.8.SIGN. Furthermore, each of the certificates CT.0, . . . , CT.8 comprises the parent certificate identifier CT.0.PID, . . . , CT.8.PID, which corresponds to the certificate identifier CT.0.ID, . . . , CT.8.ID of the parent certificate. In particular, the parent certificate identifier CT.0.PID, CT.8.PID may be identical with the certificate identifier CT.0.ID, . . . , CT.8.ID of the parent certificate. Alternatively, parent certificate identifier CT.0.PID, CT.8.PID may comprise the certificate identifier CT.0.ID, . . . , CT.8.ID of the parent certificate, or vice versa. For each of the public keys CT.0.PUBK, . . . , CT.8.PUBK there is an associated private key CT.0.PRK, . . . , CT.8.PRK that is not contained within the certificate CT.0, . . . , CT.8. The private keys CT.0.PRK, . . . , CT.8.PRK might be stored within the certified entities so that they cannot be accessed from outside the certified entity.

In this embodiment, the structure of the certificate tree is encoded in the parent certificate identifiers CT.0.PID, CT.8.PID. For example, the parent certificate identifier CT.1.PID of the child certificate CT.1 corresponds to the certificate identifier CT.0.ID of the parent certificate CT.0.

In this embodiment, the certificates CT.0, . . . , CT.8 are signed by an external certificate authority CA. In particular, the certificate authority CA creates a signature CT.0.SIGN, . . . , CT.8.SIGN by signing a combination of the certificate identifier CT.0.ID, . . . , CT.8.ID, the parent certificate identifier CT.0.PID, . . . , CT.8.PID and the public key CT.0.PUBK, CT.8.PUBK of the respective certificate CT.0, . . . , CT.8 with its private key CA-PRK.

Figure 16:
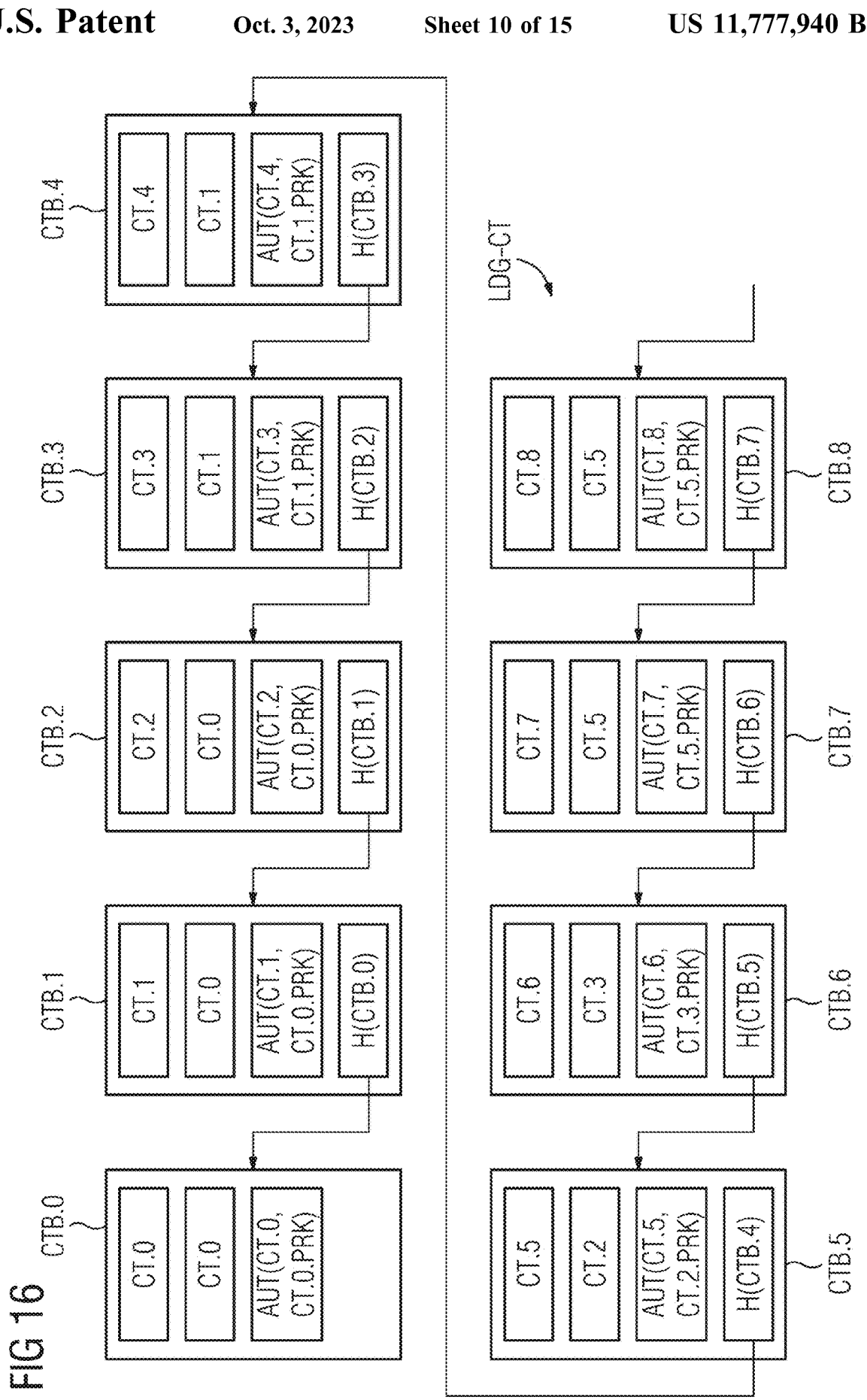
FIG. 16 shows an access ledger.

To store that a parent certificate has actually granted (direct) authorization to another certificate, an access ledger LDG-CT can be used. FIG. 16 displays an embodiment of an access ledger comprising linked certificate blocks CTB-0, . . . , CTB-8. In this embodiment, each of the linked certificate blocks CTB-0, . . . , CTB-8 comprises a certificate CT.0, . . . , CT.8, the parent certificate of the respective certificate CT.0, CT.8, authorization information AUT, and a hash value H(CTB-0), . . . , H(CTB-8) of the previous certificate block CTB-0, . . . , CTB-8 in the access ledger. For example, the certificate block CTB-3 comprises the certificate CT.3, the parent certificate CT.1 of the certificate CT.3, the authorization information AUT(CT.3, CT.1.PRK) and the hash value H(CTB-2) of the previous certificate block CTB-2 in the access ledger LDG-CT.

The first block CTB-0 is the only certificate block in the access ledger without a previous certificate block, so that the first certificate block CTB-0 does not contain a hash value of a previous certificate block.

In the displayed embodiment of a ledger LDG-CT, each certificate block CTB-0, . . . , CTB-8 of the ledger LDG-CT (except the first certificate blocks CTB-0) has exactly one preceding certificate block, and each certificate block CTB-0, . . . , CTB-8 of the ledger LDG-CT (except the last certificate block) is the parent for exactly one other block. Another word for the displayed and described ledger LDG-CT is "blockchain". Alternatively, the ledger LDG-CT can also comprise sidechains. Alternatively, the structure of the ledger LDG-CT can be a tree instead of a chain, another word for such a ledger is "blocktree". Alternatively, the structure of the ledger LDG-CT can be a directed acyclic graph, another word for such a ledger is "tangle".

In this embodiment, all certificates CT.0, . . . , CT.8 of the certificate tree are stored in successive blocks in the access ledger. It is also possible that there are other datasets stored in blocks between the certificate blocks CTB-0, . . . , CTB-8 corresponding to the certificates CT.0, . . . , CT.8 of the certificate blocks. In particular, the other datasets can be certificates from other certificate trees not related to the certificate tree formed by the certificates CT.0, . . . , CT.8.

In this embodiment, the authorization information AUT is a function of the certificate being authorized and of the private key corresponding to the certificate authorizing the certificate being authorized, which is the parent certificate. This means that the authorization information AUT has to be created by the entity to which the parent certificate belongs to, because only this entity has access to the private key. In other words, the entity to which the parent certificate belongs to has to create the block CTB.0, . . . , CTB.8 and to include the block into the access ledger LDG-CT. In this embodiment, the authorization information is a signature of the certificate being authorized signed with the private key of the parent certificate, so that the authorization information can be verified using the public key of the parent certificate.

Advantageously each of the certificate blocks CTB-0, . . . , CTB-8 furthermore comprises a timestamp indicating the creation time of the certificate CT.0, . . . , CT.8 comprised by the certificate block CTB-0, . . . , CTB-8.

Advantageously, each of the certificate blocks CTB-0, . . . , CTB-8 can comprise a dataset indicating whether authorization to the corresponding certificate CT.0, . . . , CT.8 is granted or revoked, so that it is possible to determine whether an authorization is revoked by searching through the access ledger.

TABLE C

Accessing a microservice - Token

| | |
|---|---|
| C.1 | public microservice::get_data(req_cred, pub_key): |
| C.2 | if req_cred in self.acc_creds: |
| C.3 | if (pub_key = Nothing): |
| C.4 | return decrypt(data, self.private_key) |
| C.5 | else: |
| C.6 | return encrypt(decrypt(data, self.private_key), pub_key) |
| C.7 | public microservice::get_data(req_cred): |
| C.8 | return self.get_data(req_cred, Nothing) |

Table C shows pseudocode for accessing the medical dataset DS, wherein the access credentials ACR-1, ACR-2 and the request credentials RCR.1, RCR.2 are tokens. In this embodiment, there are two different versions of the function "get_data", one taking as a parameter the request credentials RCR.1, RCR.2, and one taking as parameters the request credentials RCR.1, RCR.2 and a public key. In code lines C.7 and C.8, the first version of the function "get_data" calls the second version of the function "get_data", using an empty public key. In code line C.2, it is checked whether the request token "req_cred" matches one of the access tokens "acc_creds" stored in the microservice, only if they match the medical dataset is decrypted and returned. The decryption of the data in lines C.4 and C.6 is an asymmetrical decryption using the private key stored in the microservice MS. If a public key was given as an additional parameter, in code lines C.5 and C.6 the medical dataset DS will first be decrypted, and encrypted again with the given public key in order to prevent an ears dropper to intercept the communication. If no public key was given as an additional parameter, in code lines C.3 and C.4 the medical dataset DS will be decrypted and sent as plain text. In general, it is also possible to provide only the possibility to get the date with a public key to increase the security.

It is also possible not to store the access token in plain text, but a hash of the access token to have a higher level of security. In this case the algorithm has to compare the stored hash of the access token with the hash of the given request token.

TABLE D

Accessing a microservice - Certificates

| | |
|---|---|
| D.1 | public microservice::get_data(req_cred): |
| D.2 | certificate current_cert = req_cred |
| D.3 | certificate parent_cert = current_cert.parent( ) |
| D.4 | while current_cert != parent_cert |
| D.5 | if verify(current_cert.data( ), current_cert.hash ( ), parent_cert.pub_key( )) = False: |
| D.6 | return error |
| D.7 | if match(current_cert, acc_creds): |
| D.8 | return decrypt(data) |
| D.9 | else: |
| D.10 | current_cert = parent_cert |
| D.11 | parent_cert = current_cert.parent() |
| D.12 | return error |

Table D shows the access to a medical dataset using certificates as credentials in the case the access certificate ACC-CERT belongs to the accessing entity AE, and the microservice comprises a copy of the access certificate ACC-CERT as access credentials ACR.1, ACR.2 stored in the variable array "acc_". The function iteratively goes through the tree of certificates until the origin node has been reached (for the origin node it is true that origin.parent( )=origin). In this embodiment a certificate tree according to FIG. 14 is used, so the function "verify" checks whether the signature of the current certificate was actually created by the parent certificate. If alternatively a certificate tree according to FIG. 15 and an access ledger LDG-CT according to FIG. 16 is used, the function "verify" checks the publically available access ledger in order to check whether an authorization was given from the parent certificate to the current certificate, and optionally also that the authorization has not been revoked in the access ledger. The function "match" checks whether the current certificate and one of the access certificates ACC-CERT match, e.g. by comparing the current certificate and the access certificates ACC-CERT, or by comparing certain parts of the current certificate and certain parts of the access certificates ACC-CERT.

In the case the access certificate ACC-CERT belongs to the microservice, and wherein the access certificate ACC-CERT is directly authorized by another certificate AE.CT belonging to the accessing entity AE, the pseudocode of table D can also be used if replacing the code line D.7 by "if match(current_, acc_cred.parent( )):".

Figure 17:
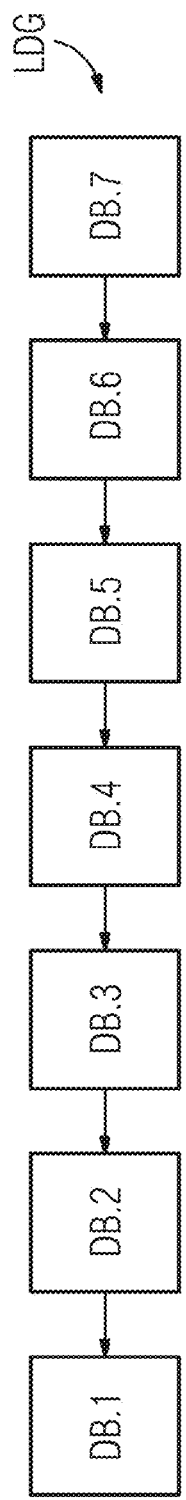
FIG. 17 shows a blockchain
Figure 18:
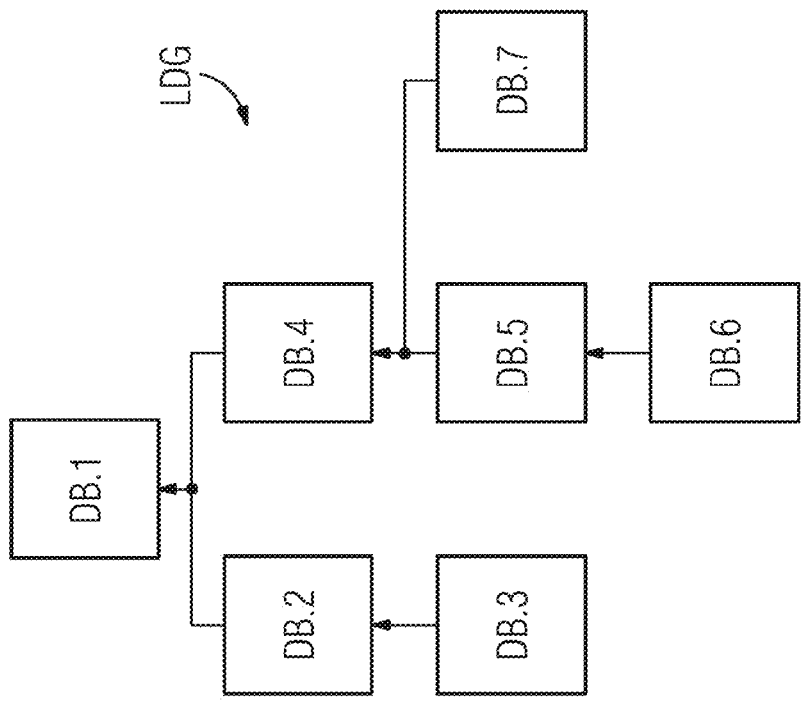
FIG. 18 shows a blocktree.
Figure 19:
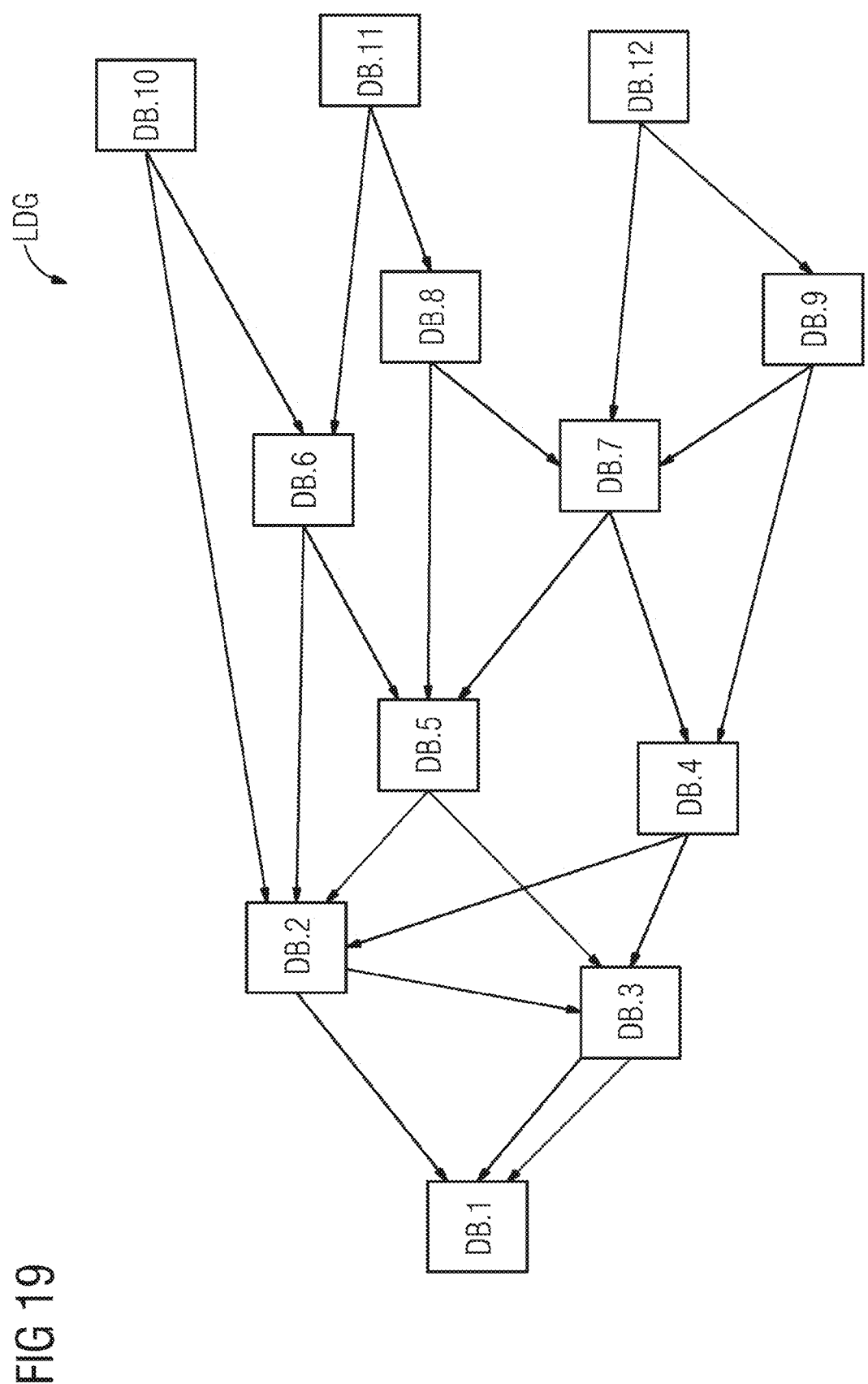
FIG. 19 shows a tangle
Figure 20:
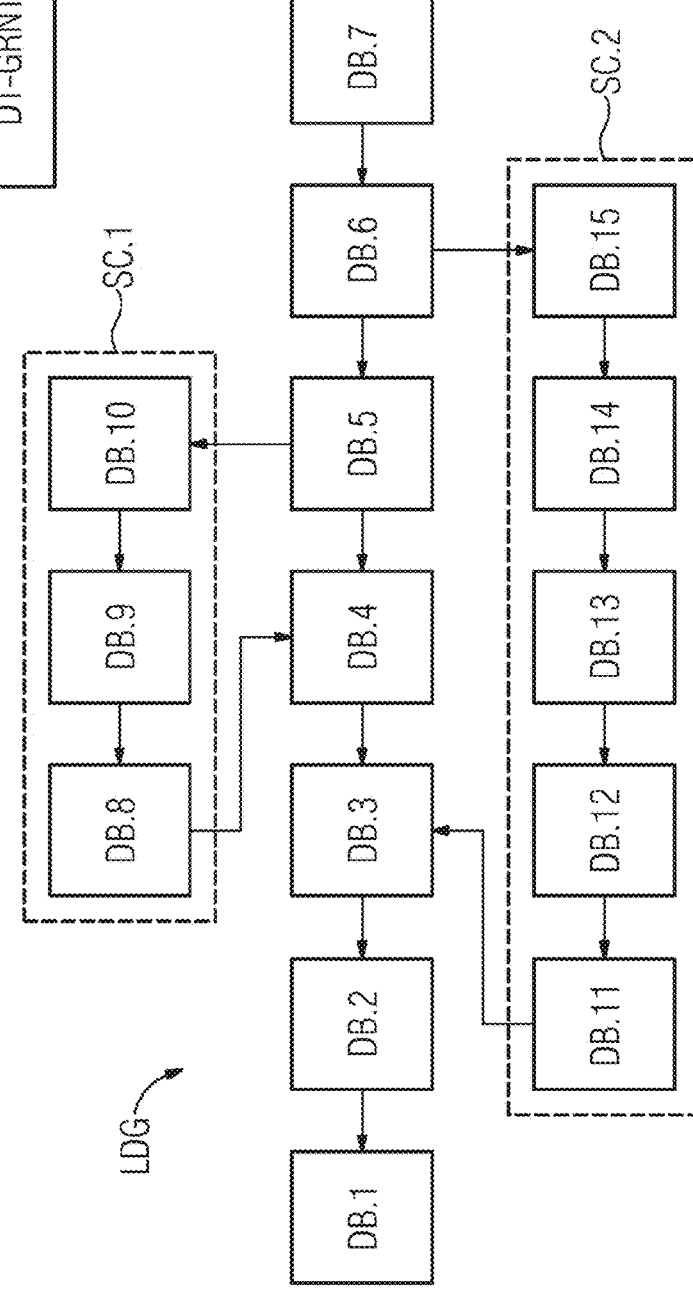
FIG. 20 shows a blockchain with sidechains.

FIG. 17 displays a first embodiment of a ledger LDG comprising blocks DB.1, . . . , DB.7, FIG. 18 displays a second embodiment of a ledger LDG comprising blocks DB.1, . . . , DB.7, FIG. 19 displays a third embodiment of a ledger LDG comprising blocks DB.1, . . . , DB.12, FIG. 20 displays a fourth embodiment of a ledger LDG comprising blocks DB.1, . . . , DB.15. The ledger LDG can be a microservice ledger LDG-MS, in this case the blocks DB.1, . . . , DB.15 or a subset of the blocks DB.1, . . . , DB.15 are a microservice MS.1, . . . , MS.4, FMS or a microservice block MSB.1, . . . , MSB.4, FMSB. The ledger LDG can also be an access ledger LDG-CT, in this case the blocks DB.1, . . . , DB.15 or a subset of the blocks DB.1, . . . , DB.15 are a certificate block CTB.0, . . . , CTB.1. The first embodiment is a blockchain, the second embodiment is a blocktree, the third embodiment is a tangle, and the fourth embodiment is a blockchain comprising two sidechains SC.1, SC.2, each sidechain SC.1, SC.2 being a blockchain.

In all three embodiments of a ledger LDG, an arrow going from a first data block DB.1, . . . , DB.15 to a second data block DB.1, . . . , DB.15 means that the first data block DB.1, . . . , DB.15 comprises a hash value based on the second data block DB.1, . . . , DB.15. Every one of the four embodiments comprises a genesis data block DB.1, which does not comprise hash information to another data block DB.2, . . . , DB.15. An alternative name for the genesis data block DB.1 is root data block.

In the first and in the second embodiment, every data block except the genesis data block DB.1 comprises one hash value of another block DB.2, . . . , DB.15, in other words for each data block DB.2, . . . , DB.15 except the genesis data block DB.1 there is exactly one outgoing arrow.

In the third embodiment, every data block DB.2, . . . , DB.15 except the genesis data block DB.1 comprises one hash values of another blocks DB.2, . . . , DB.15, in other words for each data block DB.2, . . . , DB.15 except the genesis data block DB.1 there are exactly two outgoing arrows. It is possible that the two outgoing errors point to the same other data block DB.1, . . . , DB.15, which is illustrated for the data block DB.3 in FIG. 19, in other words the two hash values of the data block DB.3 are based both on the data block DB.1. It is also possible to use another integer number of outgoing arrows or hash values, this number may be the same number for all data blocks DB.2, . . . , DB.15 except the genesis data block, alternatively the number may differ for different data blocks DB.2, . . . , DB.15.

Figure 21:
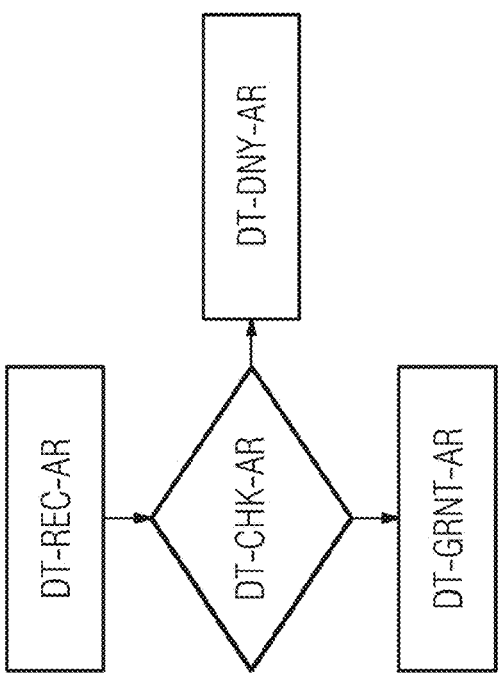
FIG. 21 shows an embodiment for a method for accessing information stored in a digital twin.

FIG. 21 shows a flowchart of an embodiment of a method for accessing information stored in a digital twin DT, wherein the digital twin DT comprises information about a real-world source, wherein a profile DP.1, DP.2, DP.3 is assigned to the digital twin DT and wherein the profile DP.1, DP.2, DP.3 defines access to a subset of the information stored in the digital twin DT, wherein the profile DP.1, DP.2, DP.3 is configurable by the real-world source.

The first step of the displayed embodiment of the method for accessing information stored in a digital twin DT is receiving DT-REC-AR an access request to the subset of information stored in the digital twin DT by a requesting entity RE.

The second step of the displayed embodiment of the method for accessing information stored in a digital twin DT is performing a check if the requesting entity RE is subject to the profile DP.1, DP.2, DP.3.

The second step of the displayed embodiment of the method for accessing information stored in a digital twin DT is granting access DT-GRN-AR or denying access DT-DNY-AR to the subset of information stored in the digital twin DT depending on the result of the check. In particular, access is granted if the result of the check is positive, and access is denied of the result of the check is negative.

Figure 22:
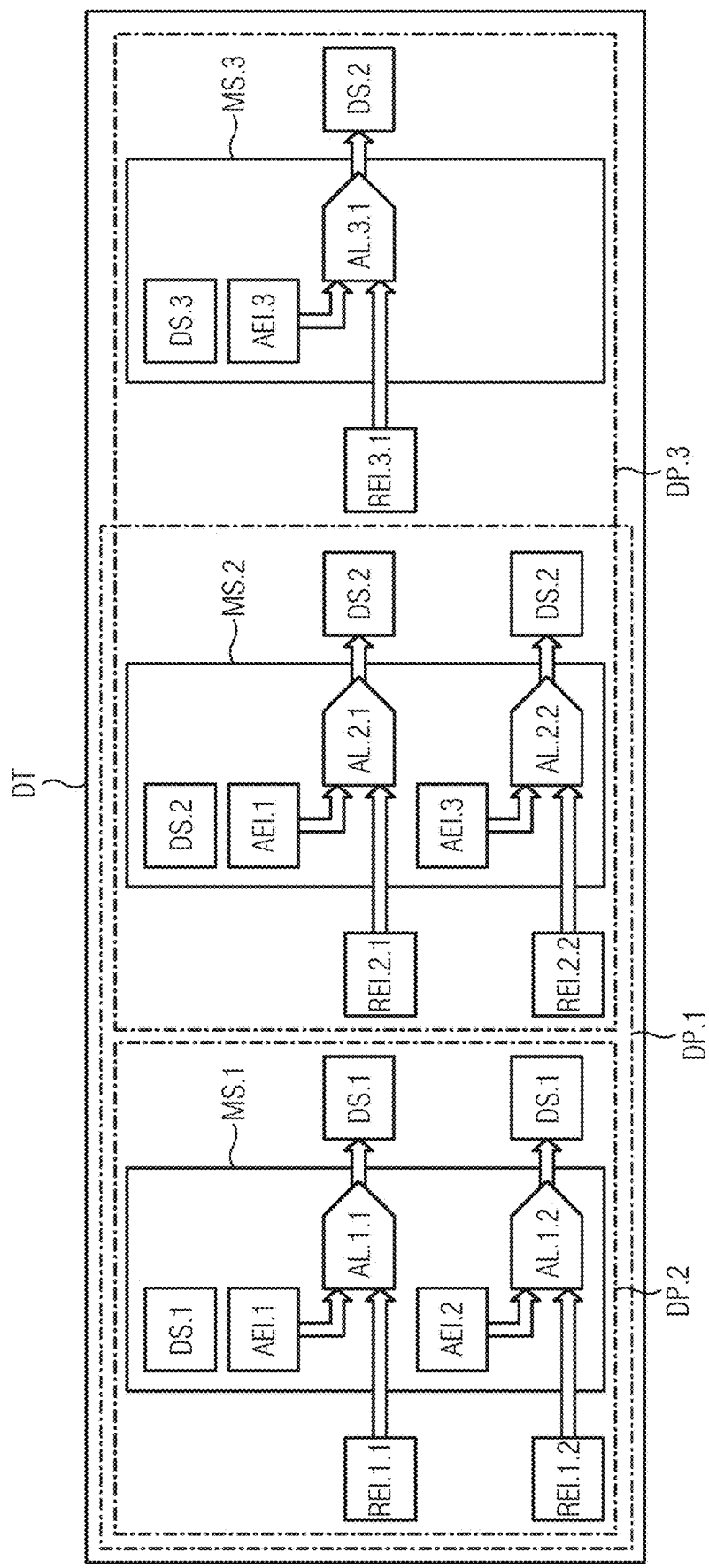
FIG. 22 shows a digital twin.

FIG. 22 shows an embodiment of a digital twin DT. In this embodiment, the digital twin DT comprises information about a real-world source which is a patient PAT, wherein the information is contained as medical datasets DS.1, DS.2, DS.3 in microservices MS.1, MS.2, MS.2. Each of the microservices MS.1, MS.2, MS.3 comprises at least one accessing entity information AEI.1, AEI.2, AEI.3 and at least one access logic AL.1.1, AL.1.2, AL.2.1, AL.2.2, AL.3.1 based on the at least one accessing entity information. The access logic AL.1.1, AL.1.2, AL.2.1, AL.2.2, AL.3.1 can be used to grant access to the medical datasets DS.1, DS.2, DS.2 contained in the microservices based on requesting entity information REI.1.1, REI.1.2, REI.2.1, REI.2.2, REI.3.1 as displayed in FIG. 11.

In this embodiment, a profile DP.1, DP.2, DP.3 defines access to the information of a subset of microservices MS.1, MS.2, MS.3 of the digital twin. In particular, a profile DP.1, DP.2, DP.3 is based on an accessing entity information AEI.1, AEI.2, AEI.3 and defines access to the information of the subset of microservices MS.1, MS.2, MS.3 which comprise the accessing entity information AEI.1, AEI.2, AEI.3 the profile DP.1, DP.2, DP.3 is based on. In this embodiment, the profile DP.1 is based on the accessing entity information AEI.1 and defines access to the microservices MS.1 and MS.2, which both comprise the accessing entity information AEI.1. Furthermore, the profile DP.2 is based on the accessing entity information AEI.2 and defines access to the microservice MS.1, which comprises the accessing entity information AEI.2. Furthermore, the profile DP.3 is based on the accessing entity information AEI.3 and defines access to the microservices MS.2 and MS.3, which both comprise the accessing entity information AEI.3.

In order to include further information into the digital twin DT so that a certain profile DP.1, DP.2, DP.3 defines access to this further information, a further microservice has to be created comprising the accessing entity information AEI.1, AEI.2, AEI.3 the certain profile DP.1, DP.2, DP.3 is based on. In order to change the subset of information a certain profile DP.1, DP.2, DP.3 defines access to, the accessing entity information AEI.1, AEI.2, AEI.3 of the corresponding one or more microservice MS.1, MS.2, MS.3 has to be removed or altered, by changing the accessing entity information AEI.1, AEI.2, AEI.3 directly within the microservice MS.1, MS.2, MS.3, or by adding a further microservice comprising the updated accessing entity information AEI.1, AEI.2, AEI.3 and invalidating the corresponding one or more microservice MS.1, MS.2, MS.3.

Figure 23:
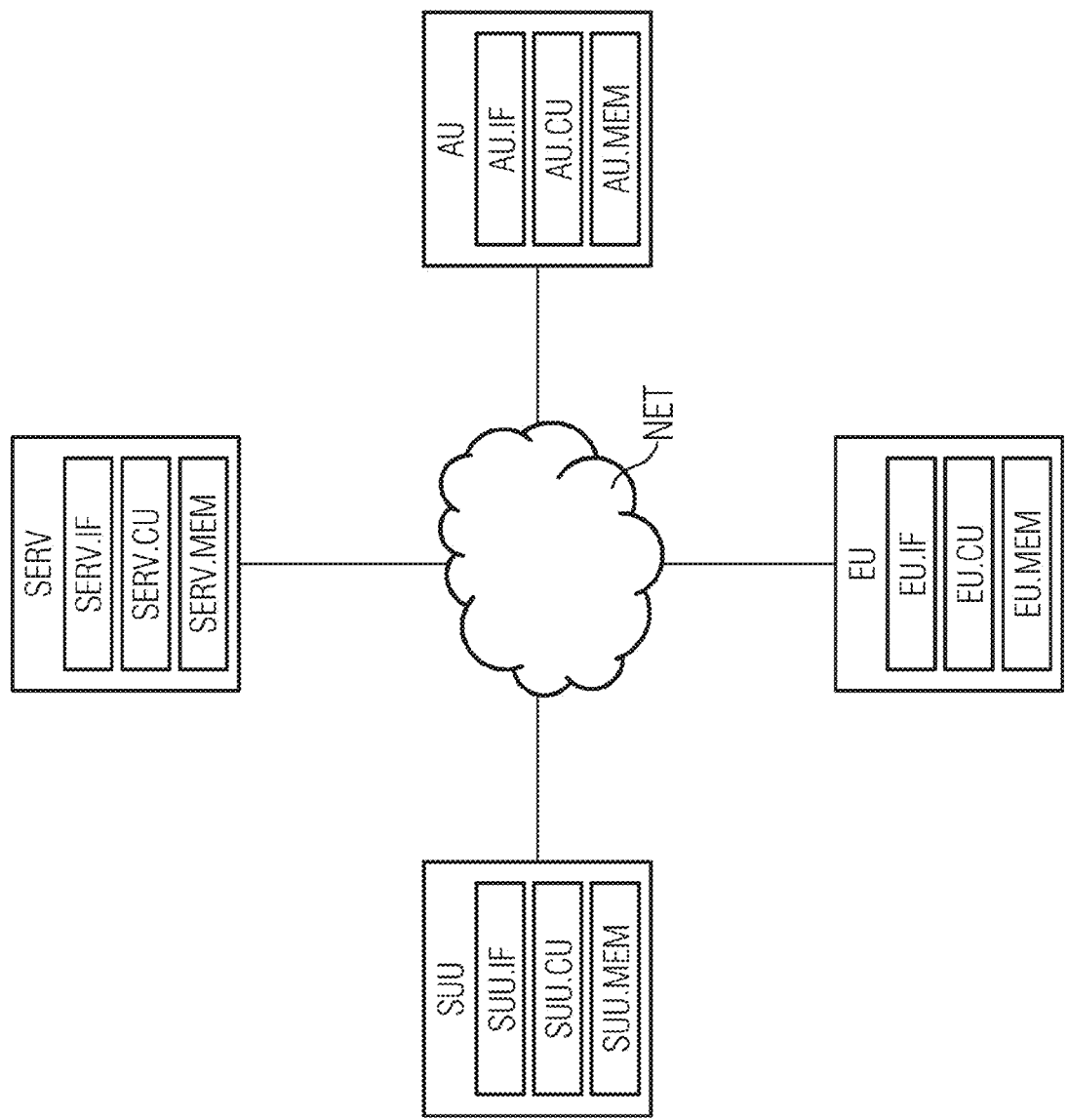
FIG. 23 shows a setting-up unit, an enhancing unit and an accessing unit.

FIG. 23 shows a system comprising a set-up unit SUU, and enhancing unit EU, an access unit AU (which can be identical to a digital twin accessing unit), and a server SERV, which are connected by a network NET. The set-up unit SUU comprises an interface SUU.IF, a calculation unit SUU.CU and a memory unit SUU.MEM. The enhancing unit comprises an interface EU.IF, a calculation unit EU.CU and a memory unit EU.MEM. The access unit AU comprises an interface AU.IF, a calculation unit AU.CU and a memory unit AU.MEM. The server SERV comprises an interface SERV.IF, a calculation unit SERV.CU and a memory unit SERV.MEM. The set-up unit SUU, the enhancing unit EU, the access unit AU and/or the server SERV can be a (personal) computer, a workstation, a virtual machine running on host hardware, a microcontroller, or an integrated circuit. As an alternative, the set-up unit SUU, the enhancing unit EU, the access unit AU and/or the server SERV can be a real or a virtual group of computers (the technical term for a real group of computers is "cluster", the technical term for a virtual group of computers is "cloud"). In particular, the set-up unit SUU can be identical with the enhancing unit EU. In particular, the set-up unit SUU can be identical with the server SERV.

An interface SUU.IF, EU.IF, AU.IF, SERV.IF can be embodied as a hardware interface or as a software interface (e.g. PCI-Bus, USB or Firewire). In general, a calculation unit SUU.CU, EU.CU, AU.CU, SERV.CU can comprise hardware elements and software elements, for example a microprocessor, a CPU (acronym for "central processing unit"), a GPU (acronym for "graphical processing unit") or a field programmable gate array. The calculation unit SUU.CU, EU.CU, AU.CU, SERV.CU can be configured for multithreading, i.e. the calculation unit SUU.CU, EU.CU, AU.CU, SERV.CU can host different calculation processes at the same time, executing the either in parallel or switching between active and passive calculation processes. A memory unit SUU.MU, EU.MU, AU.MU, SERV.MU can be e.g. non-permanent main memory (e.g. random access memory) or permanent mass storage (e.g. hard disk, USB stick, SD card, solid state disk).

In this embodiment the set-up unit SUU, the enhancing unit EU, the access unit AU and/or the server SERV are by a network NET. The network NET can be realized as a LAN (acronym for "local area network"), in particular a WiFi network, or any other local connection, e.g. via Bluetooth or USB (acronym for "universal serial bus"). The network NET can alternatively also be realized as a VPN (acronym for "virtual private network").

The displayed server SERV is configured to store the microservices MS and/or the executed the microservices MS. In particular, the displayed server SERV may be a webserver.

The setting up unit SUU, the enhancing unit EU, the accessing unit AU and the server SERV are displayed as being connected by the network NET. Alternatively it is also possible that the setting up unit SUU, the enhancing unit EU, the accessing unit AU and/or the server SERV are not connected with one or any of the other units.

Wherever not already described explicitly, individual embodiments, or their individual aspects and/or embodiments and features, can be combined or exchanged with one another without limiting or widening the scope of the described invention, whenever such a combination or exchange is meaningful and in the sense of this invention. Advantages which are described with respect to one embodiment of the present invention are, wherever applicable, also advantageous of other embodiments of the present invention.

The invention claimed is:

1. A method for setting up a microservice, the method comprising:
   receiving a medical dataset;
   receiving accessing entity information describing an accessing entity, the accessing entity information including access credentials related to the microservice, and the access credentials including an access certificate relating to ownership of a public key; and
   setting up the microservice, based on the accessing entity information, by
   encrypting the medical dataset using the public key,
   storing the encrypted medical dataset in the microservice, and
      defining access conditions to the medical dataset based on the access credentials such that the medical dataset can be accessed when the access conditions are fulfilled.

2. The method of claim 1, wherein the medical dataset relates to a patient, and wherein the accessing entity is different from the patient.

3. The method of claim 1, wherein the accessing entity information includes access credentials stored related to the microservice, wherein the the access conditions are based on the access credentials, and wherein the access conditions are fulfilled upon the access credentials being related to a requesting entity requesting access to the medical dataset.

4. The method of claim 3, wherein the access certificate belongs to the accessing entity and wherein the access certificate is related to the requesting entity upon an identity of the requesting entity being verified by the access certificate.

5. The method of claim 3, wherein the access certificate belongs to the microservice and is derived from a certificate belonging to the accessing entity, and wherein the access certificate is related to the requesting entity upon an identity of the requesting entity being verified by the certificate belonging to the accessing entity.

6. The method of claim 1, further comprising:
determining that a certificate belongs to an entity in response to the entity having access to a private key corresponding with the public key.

7. A method for accessing a medical dataset included in a microservice in an encrypted form, the method comprising:
receiving an access request to the medical dataset by a requesting entity, the access request including accessing entity information describing the accessing entity, the accessing entity information including access credentials, and the access credentials including an access certificate relating to ownership of a public key;
determining whether access conditions are met according to an access logic and the accessing entity information, the access logic defining access conditions to the medical dataset;
performing a check upon the access conditions being met; and
granting access to the medical dataset, to the requesting entity, depending on a result of the check performed.

8. The method of claim 7, wherein the access logic defines the access conditions based on the access credentials, and wherein the result of the check performed is positive, granting the requesting entity access to the medical dataset, upon the access credentials being related to request credentials related to the requesting entity.

9. The method of claim 8, wherein the request credentials are a request certificate, and wherein the result of the check performed is positive, granting the requesting entity access to the medical dataset, upon the access certificate being related to the request certificate.

10. The method of claim 9, wherein the access certificate belongs to the accessing entity and the access certificate is related to the request certificate upon the request certificate being derived from the access certificate.

11. The method of claim 9, wherein the access certificate belongs to the microservice and is directly authorized by a certificate belonging to the accessing entity, and wherein the access certificate is related to the request certificate upon the request certificate being derived from the certificate belonging to the accessing entity.

12. The method of claim 9, wherein the access certificate and the request certificate are documented in an access ledger, and wherein the access ledger regulates relationships between certificates.

13. The method of claim 8, wherein the result of the check performed is positive upon the request credentials matching the access credentials.

14. A method for accessing information stored in a digital twin, the method comprising:
receiving an access request requesting access to a subset of information stored in the digital twin by a requesting entity, the digital twin including multiple microservices storing information about a real-world source and a profile assigned to the digital twin, the profile defining access to the subset of the information stored in the digital twin via accessing entity information including an access certificate relating to ownership of a public key;
performing a check upon the requesting entity being subject to the profile; and
granting access to the subset of information in the digital twin depending on a result of the check performed, wherein
the information about the real-world source is a medical dataset, and
the profile is configurable by the real-world source.

15. The method of claim 14, wherein the information is contained by the multiple microservices in encrypted form and the subset of the information is contained by a subset of the multiple microservices.

16. The method of claim 15, wherein the multiple microservices include access logic for the information contained by the multiple microservices, and wherein the profile defines that access logic of the subset of the multiple microservices grant the requesting entity access to the subset of information upon the requesting entity being subject to the profile.

17. The method of claim 16, wherein the access logic of the subset of the multiple microservices are based on the accessing entity information describing a same accessing entity.

18. The method of claim 14, wherein the granting access to the subset of information comprises:
receiving an access request to the medical dataset by the requesting entity;
performing a check upon access conditions being met by the requesting entity; and
granting access to the medical dataset, to the requesting entity, depending on a result of the check performed.

19. A non-transitory computer readable medium storing a computer program, the computer program being loadable into a memory of a computer system and including program code sections that, when executed, cause the computer system to:
receive a medical dataset;
receive accessing entity information describing an accessing entity, the accessing entity information including access credentials related to a microservice, and the access credentials including an access certificate relating to ownership of a public key; and
set up the microservice, based on the accessing entity information, by
encrypting the medical dataset using the public key,
storing the encrypted medical dataset in the microservice, and
defining access conditions to the medical dataset based on the access credentials such that the medical dataset can be accessed when the access conditions are fulfilled.

20. A non-transitory computer readable medium storing a computer program, the computer program being loadable into a memory of a computer system and including program code sections that, when executed, cause the computer system to:

receive an access request to a medical dataset by a requesting entity, the access request including accessing entity information describing the accessing entity, the accessing entity information including access credentials, and the access credentials including an access certificate relating to ownership of a public key;

determine whether the access conditions are met according to an access logic and the accessing entity information, the access logic defining access conditions to the medical dataset;

perform a check upon the access conditions being met; and grant access to the medical dataset, to the requesting entity, depending on a result of the check performed.

\* \* \* \* \*